United States Patent
McCullough et al.

(10) Patent No.: US 11,904,143 B2
(45) Date of Patent: Feb. 20, 2024

(54) TORQUE DRIVEN DRUG DELIVERY DEVICE

(71) Applicant: AMGEN INC., Thousand Oaks, CA (US)

(72) Inventors: Adam B. McCullough, Westlake Village, CA (US); Ronald Forster, Simi Valley, CA (US); Joseph Michael Iglesias, Santa Monica, CA (US); Matias Melander, Copenhagen (DK); Rasmus Øhlenschlaeger, Kobenhavn V (DK); Christian Plambech, Soeborg (DK); Lars Stenholt, Humlebaek (DK); Bjarke Lykke Ludvig Svendsen, Slagelse (DK)

(73) Assignee: AMGEN INC., Thousand Oaks, CA (US)

( * ) Notice: Subject to any disclaimer, the term of this patent is extended or adjusted under 35 U.S.C. 154(b) by 1043 days.

(21) Appl. No.: 16/609,466

(22) PCT Filed: Jun. 4, 2018

(86) PCT No.: PCT/US2018/035816
§ 371 (c)(1),
(2) Date: Oct. 30, 2019

(87) PCT Pub. No.: WO2018/226565
PCT Pub. Date: Dec. 13, 2018

(65) Prior Publication Data
US 2023/0138654 A1 May 4, 2023

Related U.S. Application Data

(60) Provisional application No. 62/516,762, filed on Jun. 8, 2017.

(51) Int. Cl.
*A61M 5/31* (2006.01)
*A61M 5/315* (2006.01)
*A61M 5/20* (2006.01)

(52) U.S. Cl.
CPC ............ *A61M 5/3145* (2013.01); *A61M 5/20* (2013.01); *A61M 5/31583* (2013.01); *A61M 2005/3143* (2013.01)

(58) Field of Classification Search
CPC .. A61M 5/3145; A61M 5/20; A61M 5/31583; A61M 2005/3143
See application file for complete search history.

(56) References Cited

U.S. PATENT DOCUMENTS 4,043,335 A * 8/1977 Ishikawa ............. A61M 5/3145
604/243
4,638,809 A 1/1987 Kuperus
(Continued)

FOREIGN PATENT DOCUMENTS

EP 0742719 B1 12/1999
EP 0857460 B1 8/2001
(Continued)

OTHER PUBLICATIONS

Chinese Patent Application No. 2018800367426, First Office Action, dated Jun. 29, 2021.
(Continued)

*Primary Examiner* — Tasnim Mehjabin Ahmed

(57) ABSTRACT

An injector includes a housing having a syringe assembly and an actuating mechanism at least partially disposed within the housing. The syringe assembly includes a syringe barrel that stores a medicament to be injected into a user, a needle assembly, and a filter member disposed adjacent to the needle assembly. The actuating mechanism is operatively coupled to the syringe assembly and includes a torque spring that exerts a torque to urge the medicament through (Continued)

the filter member to be injected into the user. The actuating mechanism further includes a damper mechanism that exerts an opposing force to dampen the motion exerted by the torque spring.

19 Claims, 12 Drawing Sheets

(56) References Cited

U.S. PATENT DOCUMENTS

| | | | |
|---|---|---|---|
| 5,807,344 | A | 9/1998 | Iwasaki |
| 5,936,061 | A | 8/1999 | Andersson et al. |
| 6,258,068 | B1 | 7/2001 | Kirchhofer et al. |
| 6,270,479 | B1 | 8/2001 | Bergens et al. |
| 6,371,939 | B2 | 4/2002 | Bergens et al. |
| 6,554,803 | B1 | 4/2003 | Ashman |
| 6,770,052 | B2 | 8/2004 | Hill et al. |
| 6,793,646 | B1 | 9/2004 | Giambattista et al. |
| 6,796,965 | B2 | 9/2004 | Dumaresq-Lucas et al. |
| 7,125,395 | B2 | 10/2006 | Hommann et al. |
| 7,128,728 | B2 | 10/2006 | Kirchhofer et al. |
| 7,357,791 | B2 | 4/2008 | Kirchhofer et al. |
| 7,449,009 | B2 | 11/2008 | Eichhorst |
| 7,731,698 | B2 | 6/2010 | Geiser et al. |
| 7,837,943 | B2 | 11/2010 | Jeong et al. |
| 7,931,625 | B2 | 4/2011 | Kirchhofer et al. |
| 7,951,113 | B2 | 5/2011 | Kohlbrenner et al. |
| 8,021,335 | B2 | 9/2011 | Lesch, Jr. |
| 8,038,649 | B2 | 10/2011 | Kronestedt |
| 8,048,037 | B2 | 11/2011 | Kohlbrenner et al. |
| 8,152,766 | B2 | 4/2012 | Karlsson et al. |
| 8,357,120 | B2 | 1/2013 | Moller et al. |
| 8,376,998 | B2 | 2/2013 | Daily et al. |
| 8,409,138 | B2 | 4/2013 | James et al. |
| 8,517,988 | B2 | 8/2013 | Smith |
| 8,562,564 | B2 | 10/2013 | Lesch, Jr. |
| 8,617,109 | B2 | 12/2013 | Kronestedt et al. |
| 8,641,669 | B2 | 2/2014 | Renz et al. |
| 8,647,303 | B2 | 2/2014 | Cowe |
| 8,690,836 | B2 | 4/2014 | Mathews et al. |
| 8,834,449 | B2 | 9/2014 | Machan et al. |
| 8,876,766 | B2 | 11/2014 | Holmqvist et al. |
| 8,905,971 | B2 | 12/2014 | Marshall et al. |
| 9,061,103 | B2 | 6/2015 | Kemp et al. |
| 9,095,657 | B2 | 8/2015 | Holmqvist |
| 9,108,002 | B2 | 8/2015 | Markussen |
| 9,119,920 | B2 | 9/2015 | Cowe |
| 9,132,241 | B2 | 9/2015 | Guillermo |
| 9,155,837 | B2 | 10/2015 | Kemp et al. |
| 9,180,258 | B2 | 11/2015 | Kemp et al. |
| 9,180,259 | B2 | 11/2015 | Lesch, Jr. |
| 9,233,214 | B2 | 1/2016 | Kemp et al. |
| 9,233,215 | B2 | 1/2016 | Hourmand et al. |
| 9,415,165 | B2 | 8/2016 | Cowe |
| 9,446,201 | B2 | 9/2016 | Holmqvist |
| 9,457,149 | B2 | 10/2016 | Kemp et al. |
| 9,474,859 | B2 | 10/2016 | Ekman et al. |
| 9,486,581 | B2 | 11/2016 | Lovell et al. |
| 9,486,588 | B2 | 11/2016 | Enggaard |
| 2001/0007062 | A1* | 7/2001 | Dumaresq-Lucas .................. A61M 5/3145 604/247 |
| 2003/0173284 | A1 | 9/2003 | Baker |
| 2004/0158226 | A1 | 8/2004 | Soo Hoo et al. |
| 2004/0241874 | A1 | 12/2004 | Abdel-Rehim |
| 2005/0154346 | A1 | 7/2005 | Green |
| 2005/0261625 | A1 | 11/2005 | Ashman |
| 2006/0065587 | A1 | 3/2006 | Shigesada et al. |
| 2006/0276753 | A1 | 12/2006 | Kronestedt et al. |
| 2006/0287630 | A1 | 12/2006 | Hommann |
| 2007/0065319 | A1 | 3/2007 | Hommann et al. |
| 2007/0167907 | A1 | 7/2007 | Deslierres et al. |
| 2007/0265568 | A1 | 11/2007 | Tsals et al. |
| 2008/0119783 | A1 | 5/2008 | Green |
| 2009/0247951 | A1 | 10/2009 | Kohlbrenner et al. |
| 2010/0049125 | A1* | 2/2010 | James ............... A61M 5/2033 604/110 |
| 2011/0021999 | A1 | 1/2011 | Kowalski, III et al. |
| 2011/0054412 | A1 | 3/2011 | Eich et al. |
| 2011/0077595 | A1 | 3/2011 | Eich et al. |
| 2011/0124106 | A1 | 5/2011 | Froman et al. |
| 2013/0072880 | A1 | 3/2013 | Finke |
| 2013/0218128 | A1 | 8/2013 | Cowe |
| 2013/0317448 | A1* | 11/2013 | Hourmand .......... A61M 5/2033 604/197 |
| 2014/0148784 | A1 | 5/2014 | Anderson et al. |
| 2014/0171871 | A1 | 6/2014 | Mathews et al. |
| 2014/0171872 | A1 | 6/2014 | Mathews et al. |
| 2014/0254303 | A1 | 9/2014 | McArthur et al. |
| 2014/0257191 | A1 | 9/2014 | Cowe |
| 2015/0051550 | A1 | 2/2015 | Holmqvist |
| 2015/0165128 | A1 | 6/2015 | Seok et al. |
| 2015/0202365 | A1 | 7/2015 | Roervig et al. |
| 2015/0209517 | A1 | 7/2015 | Brunnberg et al. |
| 2015/0247178 | A1 | 9/2015 | Mountcastle et al. |
| 2015/0258280 | A1 | 9/2015 | Kim |
| 2015/0265776 | A1 | 9/2015 | Beek et al. |
| 2015/0314076 | A1* | 11/2015 | Markussen ......... A61M 5/31551 604/211 |
| 2015/0320938 | A1 | 11/2015 | King et al. |
| 2016/0001004 | A1 | 1/2016 | Fourt et al. |
| 2016/0008541 | A1 | 1/2016 | Hirschel et al. |
| 2016/0008542 | A1 | 1/2016 | Hirschel et al. |
| 2016/0022922 | A1 | 1/2016 | Kemp et al. |
| 2016/0030681 | A1 | 2/2016 | Jones et al. |
| 2016/0038677 | A1 | 2/2016 | Kiilerich |
| 2016/0038679 | A1 | 2/2016 | Guillermo |
| 2016/0045672 | A1 | 2/2016 | Morris et al. |
| 2016/0051765 | A1 | 2/2016 | Morris et al. |
| 2016/0067418 | A1 | 3/2016 | Morris et al. |
| 2016/0067420 | A1 | 3/2016 | Higgins et al. |
| 2016/0074584 | A1 | 3/2016 | Carmel et al. |
| 2016/0074592 | A1 | 3/2016 | Pedersen et al. |
| 2016/0082196 | A1 | 3/2016 | Higgins et al. |
| 2016/0091399 | A1 | 3/2016 | Chen et al. |
| 2016/0106920 | A1 | 4/2016 | Stefansen |
| 2016/0151579 | A1 | 6/2016 | Oakley et al. |
| 2016/0235924 | A1 | 8/2016 | Soerensen et al. |
| 2016/0250417 | A1 | 9/2016 | Olson |
| 2016/0287791 | A1 | 10/2016 | Olson |
| 2016/0310874 | A1 | 10/2016 | Pathirana |

FOREIGN PATENT DOCUMENTS

| | | |
|---|---|---|
| EP | 0956155 B1 | 8/2002 |
| EP | 1287164 B1 | 10/2004 |
| EP | 0956875 B1 | 8/2005 |
| EP | 1439872 B1 | 9/2006 |
| EP | 1586342 B1 | 1/2007 |
| EP | 1586341 B1 | 1/2008 |
| EP | 1762261 B1 | 4/2008 |
| EP | 1728529 B1 | 7/2008 |
| EP | 1425566 B1 | 11/2009 |
| EP | 2192938 A1 | 6/2010 |
| EP | 2198903 A1 | 6/2010 |
| EP | 2249902 A2 | 11/2010 |
| EP | 1954337 B1 | 1/2011 |
| EP | 2218823 B1 | 8/2011 |
| EP | 2364739 A1 | 9/2011 |
| EP | 2364740 A1 | 9/2011 |
| EP | 2364741 A1 | 9/2011 |
| EP | 2370131 A1 | 10/2011 |
| EP | 2399627 A1 | 12/2011 |
| EP | 2399631 A1 | 12/2011 |
| EP | 2438939 A1 | 4/2012 |
| EP | 2468337 A1 | 6/2012 |
| EP | 2468341 A1 | 6/2012 |
| EP | 2484395 A2 | 8/2012 |
| EP | 1885414 B1 | 11/2012 |
| EP | 2526987 A2 | 11/2012 |
| EP | 2560712 A1 | 2/2013 |
| EP | 2563431 A1 | 3/2013 |
| EP | 1885415 B1 | 5/2013 |

(56) References Cited

FOREIGN PATENT DOCUMENTS

| | | | |
|---|---|---|---|
| EP | 1680160 | B1 | 7/2013 |
| EP | 2634742 | A1 | 9/2013 |
| EP | 2665501 | A1 | 11/2013 |
| EP | 2716316 | A1 | 4/2014 |
| EP | 2742962 | A2 | 6/2014 |
| EP | 2806921 | A1 | 12/2014 |
| EP | 2825228 | A1 | 1/2015 |
| EP | 2825245 | A2 | 1/2015 |
| EP | 2926853 | A1 | 10/2015 |
| EP | 2926859 | A1 | 10/2015 |
| EP | 2198906 | B1 | 1/2016 |
| EP | 2968766 | A1 | 1/2016 |
| EP | 2379135 | B1 | 2/2016 |
| EP | 2051753 | B1 | 5/2016 |
| EP | 1907033 | B1 | 8/2016 |
| EP | 3055004 | A1 | 8/2016 |
| EP | 3064241 | A1 | 9/2016 |
| EP | 3068467 | A1 | 9/2016 |
| EP | 3020433 | B1 | 1/2017 |
| EP | 2983772 | B1 | 2/2017 |
| EP | 3017837 | B1 | 2/2017 |
| JP | 2006272006 | A | 10/2006 |

OTHER PUBLICATIONS

International Search Report and Written Opinion, corresponding International Application No. PCT/US2018/035816, dated Oct. 23, 2018.

Japanese Patent Application No. 2019-561838, Notice of Reasons for Refusal, dated Feb. 22, 2022.

Second Office Action received in counterpart Chinese Patent Application No. 201880036742.6, dated Jan. 13, 2022.

Examination Report received in counterpart European Patent Application No. 18733474.3, dated Jan. 17, 2023.

Office Action received in counterpart Israel Patent Application No. 270662, dated Sep. 1, 2022.

Second Office Action received in counterpart Japanese Patent Application No. 2019-561838, dated Aug. 9, 2022.

Notification to Grant received in counterpart Chinese Patent Application No. 201880036742.6, dated Apr. 13, 2022.

Examination Report received in counterpart Australian Patent Application No. 2018282077, dated Jul. 13, 2023.

Office Action received in counterpart Japanese Patent Application No. 2022-202914, dated Oct. 17, 2023.

* cited by examiner

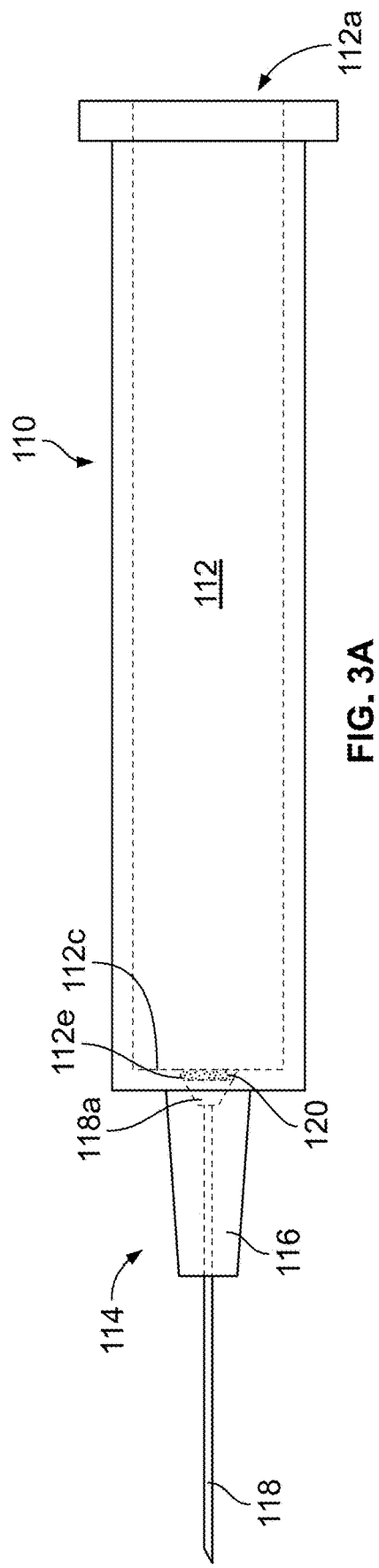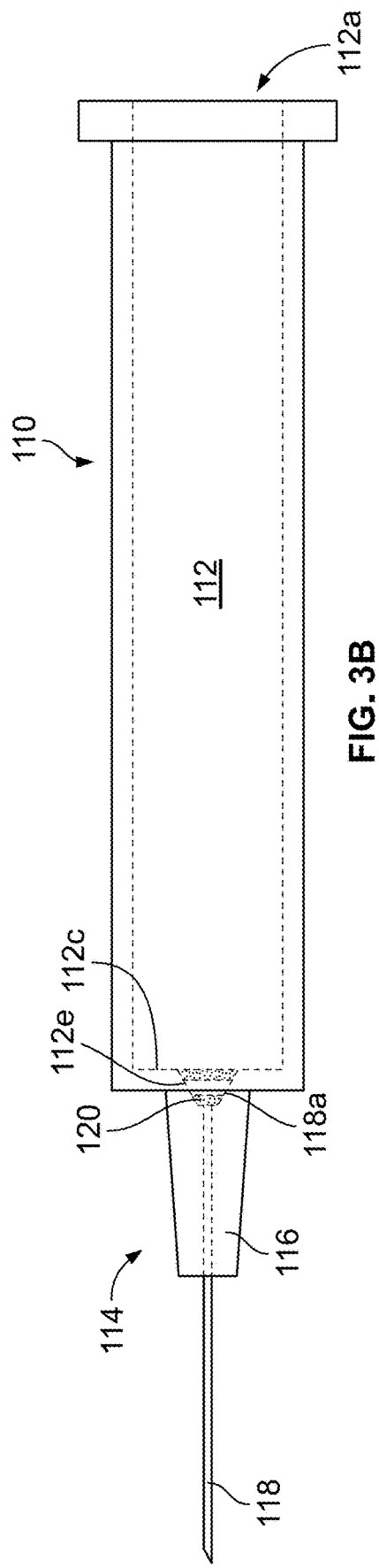

TORQUE DRIVEN DRUG DELIVERY DEVICE

CROSS-REFERENCE TO RELATED APPLICATION

This is the United States National Phase of PCT/US18/35816, filed Jun. 4, 2018, which claims the priority benefit of U.S. Provisional Patent Application No. 62/516,762, filed Jun. 8, 2017, the entire contents of each of which are hereby incorporated herein by reference.

FIELD OF THE DISCLOSURE

The present disclosure generally relates to injectors and, more particularly, to a torque driven injector optionally having a damper mechanism and a filtering device.

BACKGROUND

Autoinjectors and on-body injectors offer several benefits in delivery of medicaments and/or therapeutics. One of the benefits can include simplicity of use, as compared with traditional methods of delivery using, for example, conventional syringes.

Many injector systems use coil spring structures to provide actuation energy for functions such as needle insertion and medicament delivery. The use of springs can offer benefits of simplicity for the user and device automation, but can have certain limitations. For example, there is a linear relationship between force and displacement in linear spring actuators. To provide sufficient energy for drug delivery at the end of plunger stroke, an excessive amount of energy may be input to the system as drug delivery commences.

Further, as higher viscosity drugs are delivered via autoinjectors, requisite spring forces will likely increase. Springs with higher spring constants transmit more force per travel distance to the drug product and primary container at the beginning of travel. In many autoinjectors, an air gap is present between a plunger face and a storage portion that contains the medicament prior to its injection into a user. When the drug is to be administered, the spring urges the plunger face through the air gap towards the medicament. Because the plunger face exhibits little resistance when traversing the air gap and due to large forces urging the plunger, the plunger face may make abrupt contact with the storage portion containing the medicament. A patient may feel this excessive energy as a "slap" or similar physical "bump", as the spring driven plunger impacts the stopper of the primary container storing the drug. Further, the user may also experience a jerk, recoil, and/or a reaction force when rotational movement begins due to the abrupt change in acceleration. Such mechanical bumps can be distracting and/or disturbing to users of the injectors and can therefore impact proper dose administration. Further, the "slap" and "bump" generated by the excessive energy can potentially cause catastrophic effects, such as breakage of the primary container and drug product damage cause by shear load. Furthermore, high force springs can produce undesirably high shear rates on the drug product.

Additionally, it is possible that when pre-filled syringes are initially filled, unwanted particles may be dispersed within the medicament. These particles may complicate delivery and/or contaminate the medicament.

SUMMARY

In accordance with a first aspect, an injector includes a housing having a syringe assembly and an actuating mechanism at least partially disposed within the housing. The syringe assembly can include a syringe barrel that stores a medicament to be injected into a user, a needle assembly, and an optional filter member disposed adjacent to the needle assembly. The actuating mechanism is operatively coupled to the syringe assembly and includes a torque spring that exerts a torque that urges the medicament through the filter member to be injected into the user. The actuating mechanism further includes a damper mechanism that exerts an opposing force or torque to dampen the torque exerted by the torque spring.

In this aspect, the syringe barrel has a first end, a second end, and a longitudinal axis. The needle assembly is coupled to the second end of the syringe barrel, and includes a needle hub and a needle attached to the needle hub. The filter member restricts particles dispersed within the medicament from entering the needle assembly.

The actuating mechanism further includes a frame member, a plunger assembly that includes a threaded plunger rod and a plunger face, and a plunger rod guide. The frame member is coupled to the housing and has a threaded opening formed between a first surface and a second surface thereof. The threaded plunger rod threadably couples to the threaded opening of the frame member. The plunger face is disposed near the first end of the syringe barrel. The plunger assembly is moveable along the longitudinal axis of the syringe barrel. The plunger rod guide is coupled to the plunger assembly to guide rotational movement of the plunger assembly, and to transfer a torque. As the plunger rod guide rotates due to a torque exerted by the torque spring, the plunger assembly advances towards the syringe barrel to urge the medicament through the filter and the needle assembly.

In some approaches, the filter member is at least partially disposed within a portion of the needle hub and includes a plurality of openings to allow the medicament to pass through while restricting particles dispersed within the medicament from passing through. Any number of these openings may have a diameter of between approximately 10 µm and approximately 50 µm. The openings may be of any shape or configuration such as conical, cylindrical, etc.

In one form, the torque spring may be tightly wound, having between approximately 1 and approximately 30 turns. By using a tightly wound torque spring, a consistent amount of torque is generated throughout the actuation process. In some approaches, the threaded plunger rod and/or the threaded opening of the frame member may have a thread pitch between approximately 2 mm and approximately 6 mm, which, when combined with the tightly wound torque spring (and the damper), impart high forces on the medicament at a low velocity, thus reducing overall impact speed between the plunger face and the syringe barrel.

In some examples, the damper mechanism may include a viscous material disposed between a portion of the plunger rod guide and the housing. In other examples, the damper mechanism may alternatively be disposed between a different rotating element and the housing, a linear moving element and the housing, or two any other elements that move relative to each other. The damper mechanism includes a deformation region adapted to at least partially deform as the plunger assembly advances towards the syringe barrel. In yet other examples, the damper mechanism includes a rotating or linear damping device disposed between the plunger rod guide and the plunger assembly.

In accordance with a second aspect, a syringe assembly is provided for an injector that additionally includes a housing having an actuating mechanism at least partially disposed within the housing and being coupled to the syringe assembly. The syringe assembly includes a syringe barrel, a needle assembly, and a filter member. The syringe barrel has a first end, a second end, and a longitudinal axis, and stores a medicament to be injected into a user. The needle assembly is coupled to the second end of the syringe barrel, and includes a needle hub and a needle attached thereto. The filter member is disposed adjacent to the needle hub. The filter member restricts particles dispersed within the medicament from entering the needle assembly.

In accordance with a third aspect, an actuating mechanism is provided for an injector that additionally includes a housing having a syringe assembly at least partially disposed within the housing and being coupled to the actuating mechanism. The actuating mechanism includes a frame member, a plunger assembly, a plunger rod guide, a torque spring, and a damper mechanism. The frame member is coupled to the housing, and has a threaded opening formed between a first surface and a second surface. The plunger assembly includes a threaded plunger rod and a plunger face. The threaded rod threadably couples to the threaded opening of the frame member. The plunger face is disposed near the syringe assembly. The plunger rod guide is coupled to the plunger assembly to guide rotational movement of the plunger assembly and to transfer a torque thereto. The torque spring is coupled to the plunger rod guide to exert a torque on the plunger rod guide that causes the plunger rod guide to rotate. The damper mechanism is formed by at least a portion of the plunger rod guide or a part coupled to the plunger rod guide. Upon the torque spring exerting a torque on the plunger rod guide, the damper mechanism exerts an opposing force on the plunger rod guide to reduce an impact force and/or speed between the plunger assembly and the syringe assembly.

BRIEF DESCRIPTION OF THE DRAWINGS

The above needs are at least partially met through provision of the torque driven drug delivery device described in the following detailed description, particularly when studied in conjunction with the drawings, wherein:

FIGS. 3a and 3b illustrate cross-sectional views of example filter member placements within a syringe assembly of the torque driven injector of FIG. 1 in accordance with various embodiments;

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, a torque driven injector includes a housing, a syringe assembly containing a medicament to be injected into a user, and a rotatable actuating assembly using a torque spring to cause the medicament to be injected into the user. As the medicament passes through the syringe assembly, an optional filter mechanism may restrict any unwanted foreign particles in the medicament from being injected into the user. So configured, the filter mechanism can reliably mitigate the risk of injecting unwanted foreign particles into the user.

Further, as the actuating mechanism rotates, a damper mechanism reduces or eliminates the "slap" or "bump" that occurs when the plunger face first contacts the medicament and/or medicament storage device. The damper mechanism may also reduce the "jerk" or recoil when the mechanism is released. Accordingly, a user will not feel this sudden movement during the drug delivery process, and can comfortably and safely administer the medicament. Further, the torque spring, which uses a high number of turns, discussed in further detail below, may maintain near-constant start and end torque as compared to traditional springs and those with fewer turns. As a result, smaller autoinjectors may be used, which can increase overall user comfort.

Figure 1:
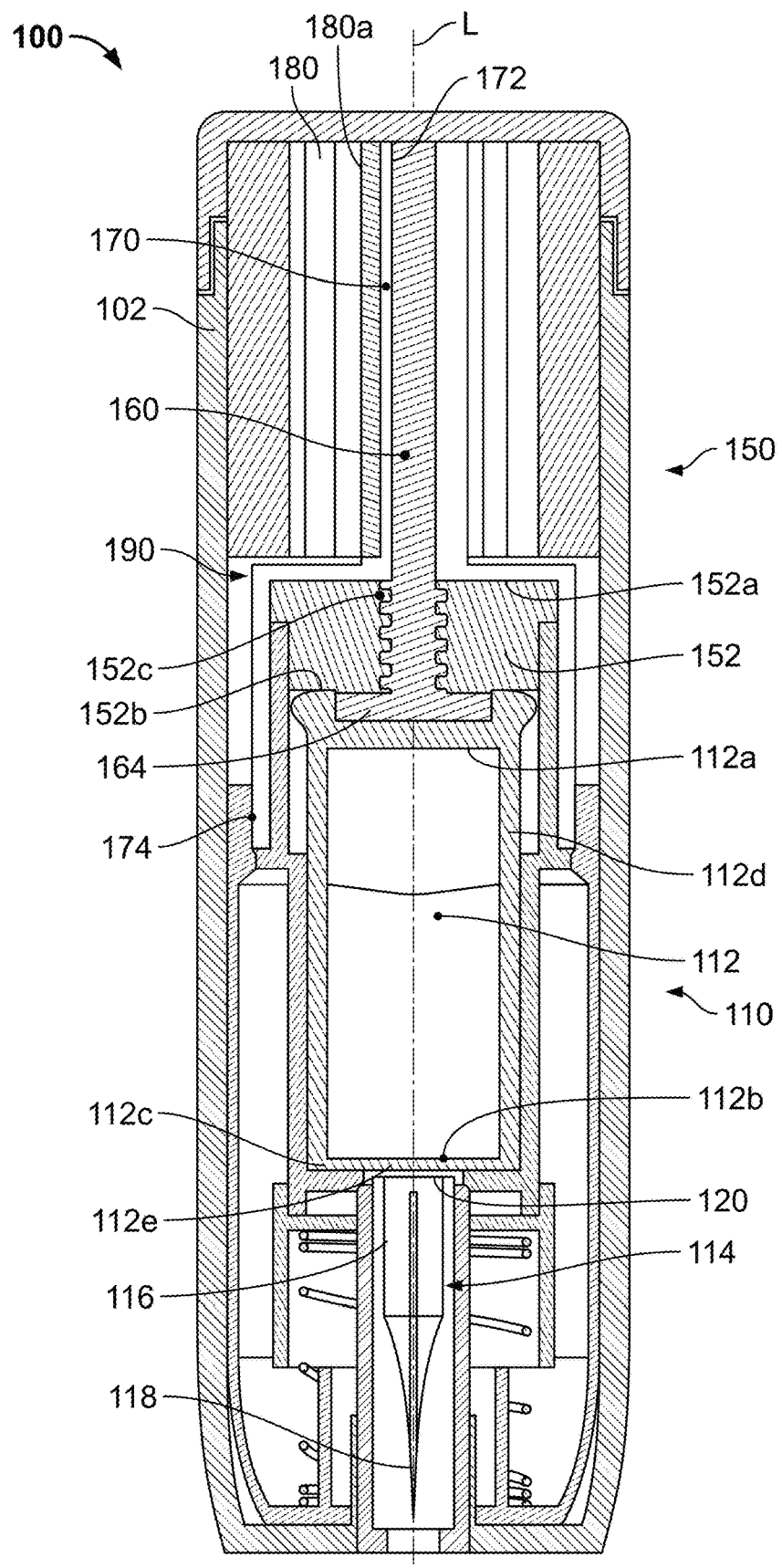
FIG. 1 illustrates an example torque driven injector having a damper mechanism and a filter member in accordance with various embodiments.

Referring now to the drawings, and in particular to FIG. 1, an example autoinjector 100 includes a housing 102 having a syringe assembly 110 and an actuating mechanism 150. At least a portion of the syringe assembly 110 and the actuating mechanism 150 are disposed within the housing 102. The syringe assembly 110 includes a syringe barrel 112, a needle assembly 114, and an optional filter member 120 disposed adjacent to the needle assembly 114. The actuating mechanism 150 includes a frame member 152, a plunger assembly 160, a plunger rod guide 170, a torque spring (e.g., a power spring) 180, and an optional damper mechanism 190.

The syringe barrel 112 stores a medicament to be injected into a user, and has a first end 112a, a second end 112b, and a longitudinal axis "L". In the illustrated example, the syringe barrel 112 further includes a base 112c and a sidewall 112d that define a cavity to store the medicament. Further, the syringe barrel 112 may include at least one opening 112e disposed through the base 112c to allow the medicament to pass into the needle assembly 114. The first end 112a of the syringe barrel 112 may be open to accommodate the plunger assembly 160, which will be described in further detail below.

It is understood that the syringe barrel 112 may be any desired shape and/or size to accommodate various quantities of medicament. In some examples, the syringe barrel 112 can be constructed from a cyclic-olefin polymer ("COP"). Other examples of materials are possible.

With reference to FIGS. 1, 3a, and 3b, the needle assembly 114 is coupled to the second end 112b of the syringe barrel 112 via any type of coupling mechanism and/or structure, and includes a needle hub 116 and a needle 118 attached thereto. The needle hub 116 defines a cavity that allows medicament to enter into the needle 118 via any number of openings 118a. The needle hub 116 is positioned below the opening 112e formed in the base 112c of the syringe barrel 112. So configured, the needle hub 116 receives the medicament as it exits the syringe barrel 112, which then enters into the needle 118 to be administered to the user. It is understood that the injector 100 may include any number of additional components such as return springs, needle shields and/or guards, and the like to assist in administering the medicament to the user. For the sake of brevity, these additional components will not be discussed in substantial detail.

With continued reference to FIGS. 1-3b, the filter member 120 is disposed adjacent to the syringe barrel 112 and the needle assembly 114. In some examples (FIG. 3a), the filter member 120 may be disposed directly within the opening 112e formed in the base 112c of the syringe barrel 112. In other examples, and as illustrated in FIG. 3b, the filter member 120 may be disposed within a portion of the cavity defined by the needle hub 116, distally beyond the base 112c of the barrel 112. In yet other examples (not illustrated), the filter member 120 may be positioned between the base 112c of the syringe barrel 112 and the needle hub 116. Alternatively, the filter member 120 may be positioned within the syringe barrel 112, and occupy substantially the entire cross-sectional area of the syringe barrel 112.

Figure 2B:
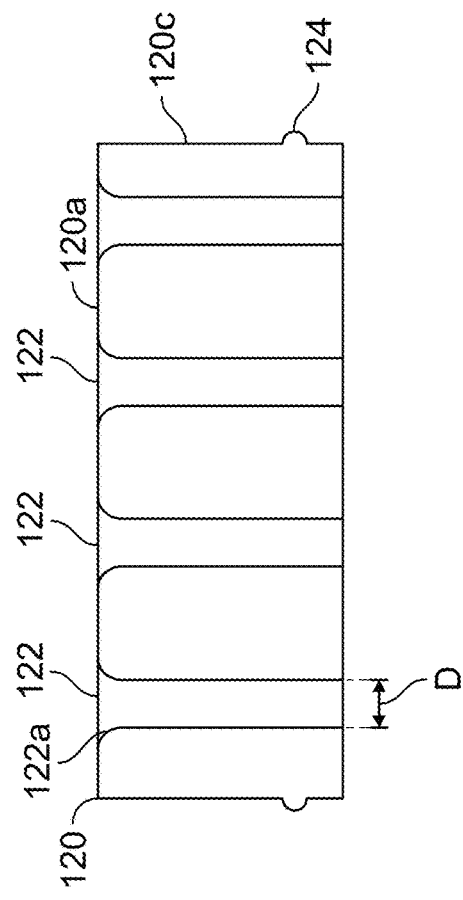
FIGS. 2b and 2c illustrate cross-sectional views of example filter member arrangements in accordance with various embodiments.
Figure 2D:
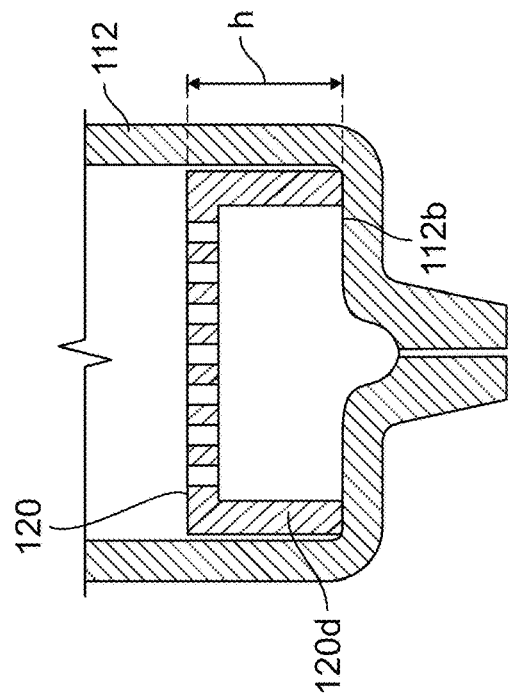
FIG. 2d illustrates a cross-sectional view of an alternate filter member arrangement where the filter member is an elevated platform in accordance with various embodiments.
Figure 2A:
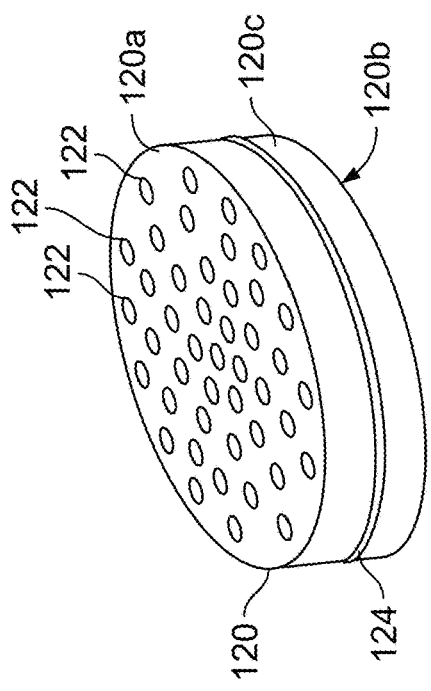
FIG. 2a illustrates a perspective view of an example filter member in accordance with various embodiments.
Figure 2C:
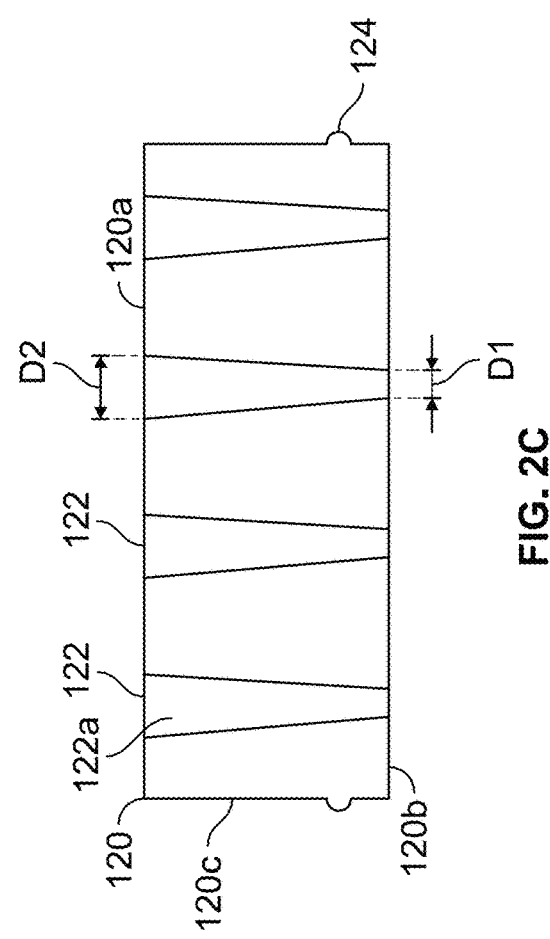
Figure 2F:
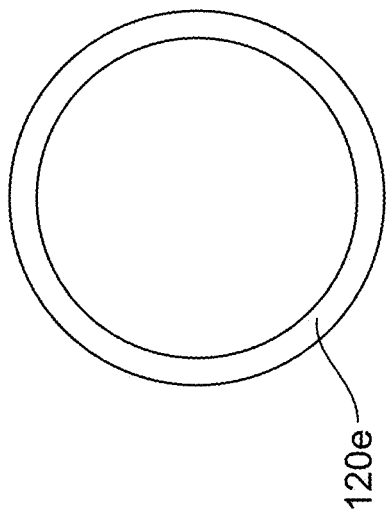
FIGS. 2e-2h illustrate views of an alternate filter member arrangement in accordance with various embodiments.

As illustrated in FIGS. 2a-2c, the filter member 120 may be generally cylindrically and/or wafer shaped. The filter member 120 may be constructed from a polymer such as polyvinylidene fluoride (PVDF), though other examples of materials are possible. The filter member 120 may include an upper surface 120a, a lower surface 120b, and a sidewall 120c connecting the upper surface 120a and the lower surface 120b. The filter member 120 also includes a number of pores or openings 122 to allow the medicament to pass through (e.g., from the opening 112e of the syringe barrel 112, through the upper surface 120a, and to the lower surface 120b) while restricting particles dispersed within the medicament from passing through. In some examples, each of the openings 122 may have a diameter, length, or other cross-sectional dimension (denoted by reference "D" in FIG. 2b) of between approximately 10 µm and approximately 50 µm, and preferably, between approximately 15 µm and approximately 30 µm. However, it is understood that the openings 122 may be dimensioned as desired in order to properly filter particles of desired sizes from the medicament.

In the illustrated example of FIG. 2b, the openings 122 are generally parallel in shape. Put another way, the diameter of the openings 122 disposed on both the upper surface 120a and the lower surface 120b are approximately equal. As such, the openings 122 are generally cylindrical in shape. It is understood, however, that the openings 122 may be of any shape such as cuboid, prismatic, etc. In this example, any particles that are larger than the dimension D will be restricted from passing through the openings 122, and will instead rest against the upper surface 120a of the filter member 120.

In some examples, and as illustrated in FIG. 2c, the diameter, length, or other cross-sectional dimension (denoted by reference "$D_2$") of the opening disposed through the upper surface 120a of the filter member 120 is larger than the opening (denoted by reference "$D_1$") disposed through the lower surface 120b. In these examples, the openings 122 may be, for example, partially conically shaped. In these examples, any particles which are larger than the dimension $D_2$ will not be able to pass therethrough, and instead will remain disposed within cavity formed by the opening 122. It is understood that any arrangement of the openings 122 illustrated in FIGS. 2b and 2c may be used separately or in combination.

In some examples, such as embodiments where a high-viscosity medicament is used, the openings disposed through the upper surface 120a of the filter member 120 is smaller than the opening disposed through the lower surface 120b. So configured, the medicament would first flow through the smaller diameter side and out through the larger diameter side, thereby exhibiting divergent flow characteristics. Accordingly, particles would not be caught or in trapped in the conical tube, thereby reducing pressure loss, which in turn may result in less power needed to expel the medicament.

The filter member 120 may also include a coupling mechanism 124 disposed on the sidewall 120c to secure the filter member 120 at the desired location within the injector 100. The coupling mechanism 124 may be formed integrally with the filter member 120, or it may be a distinct component. In the illustrated examples of FIGS. 2a-2c, the coupling mechanism 124 is an annular protrusion or ring that inserts into a corresponding notch or groove (not shown) formed in the desired component (e.g., the opening 112e formed in the base 112c of the syringe barrel 112, the needle hub 116, etc.). Other coupling mechanisms 124 are possible.

In some examples, the coupling mechanism 124 may restrict axial movement along axis L in any direction. In these examples, the coupling mechanism 124 may be a multidirectional locking tab. However, in other examples, the coupling mechanism 124 may only restrict axial movement along axis L in the downward direction, that is, when the medicament is being ejected from the injector 100. Because the syringes are pre-filled, it may not be necessary to have a multidirectional locking mechanism because such a component may increase overall costs.

In some examples and as illustrated in FIG. 2b, any number (one or more) of the openings 122 may include rounded, beveled, and/or chamfered regions 122a where the upper surface 120a forms the opening 122. So configured, the filter member 120 will not cause the larger, undesirable particles to be broken into smaller sizes when passing through the filter member 120, which may potentially allow the particle to pass through the filter member 120 and into the user.

In some examples, and as illustrated in FIG. 2d, the filter member 120 may be disposed within a portion of the syringe barrel 112. In this example, the filter member 120 includes an elevated or shelf portion 120d. so configured, the lower surface 120b of the filter 120 is disposed a distance (denoted by "h" in FIG. 2d) away from the second end 112b of the syringe barrel 112. This configuration may provide for smoother flow of the medicament when being administered to the user.

Figure 2H:
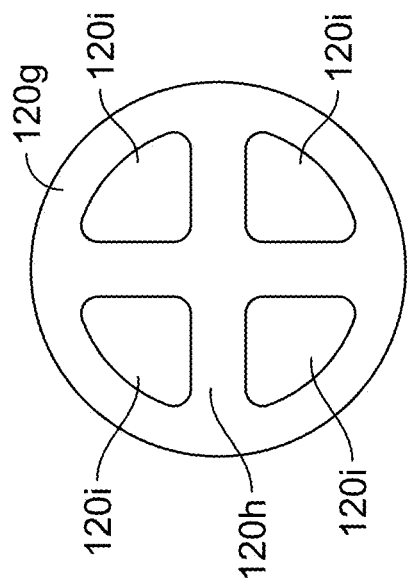
Figure 2E:
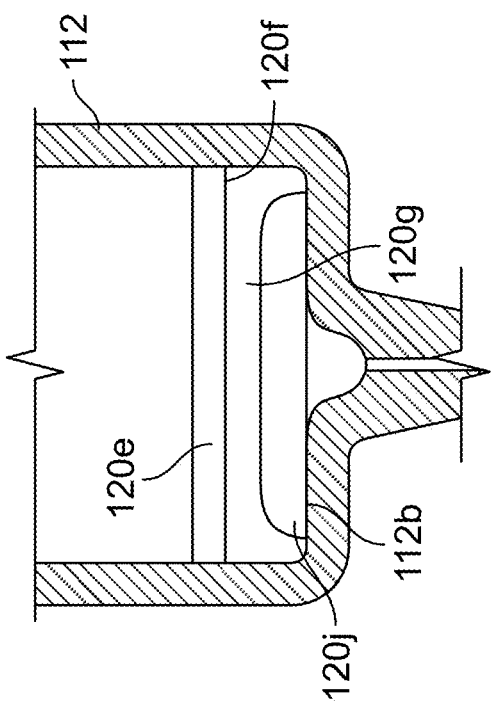
Figure 2G:
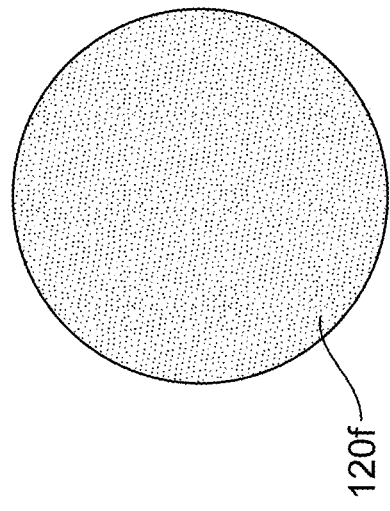

Turning to FIGS. 2e-2h, an alternate filter assembly is provided that is disposed within a portion of the syringe barrel 112. The filter assembly includes a retention ring 120e (FIG. 2f), a filter sheet 120f (FIG. 2g), and a support member 120g (FIG. 2h). The retention ring 120e is adapted to retain the filter sheet 120f in place and to restrict upward lateral movement of the filter sheet 120f. The filter sheet 120f may be porous and have a porosity to allow fluid to flow therethrough while restricting particles within the medicament. The filter sheet 120f may rest on the support member 120g, which may have a central support structure 120h in the form of a web that separates its opening into four quadrants 120i. By dividing the opening into quadrants and providing the support structure 120h, flexure of the filter sheet 120f is limited when it is under a high differential pressure, and thus will not have an impact on fluid flow. Further the support structure 120h minimizes any fluid flow-restricting surface areas. As illustrated in FIG. 2e, the support member 120g may have a raised portion 120j that acts as a relief and allows fluid flow between the individual quadrants.

Figure 4A:
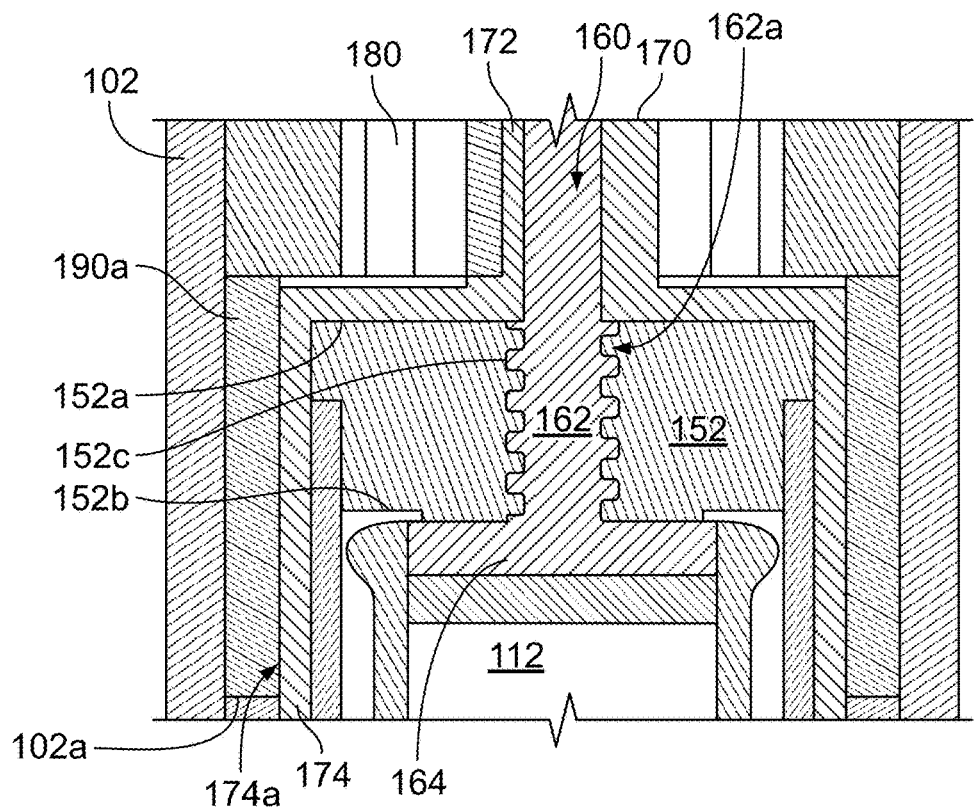
FIGS. 4a-4c illustrate cross-sectional views of a portion of example actuating mechanisms of the torque driven injector of FIG. 1 in accordance with various embodiments.
Figure 4B:
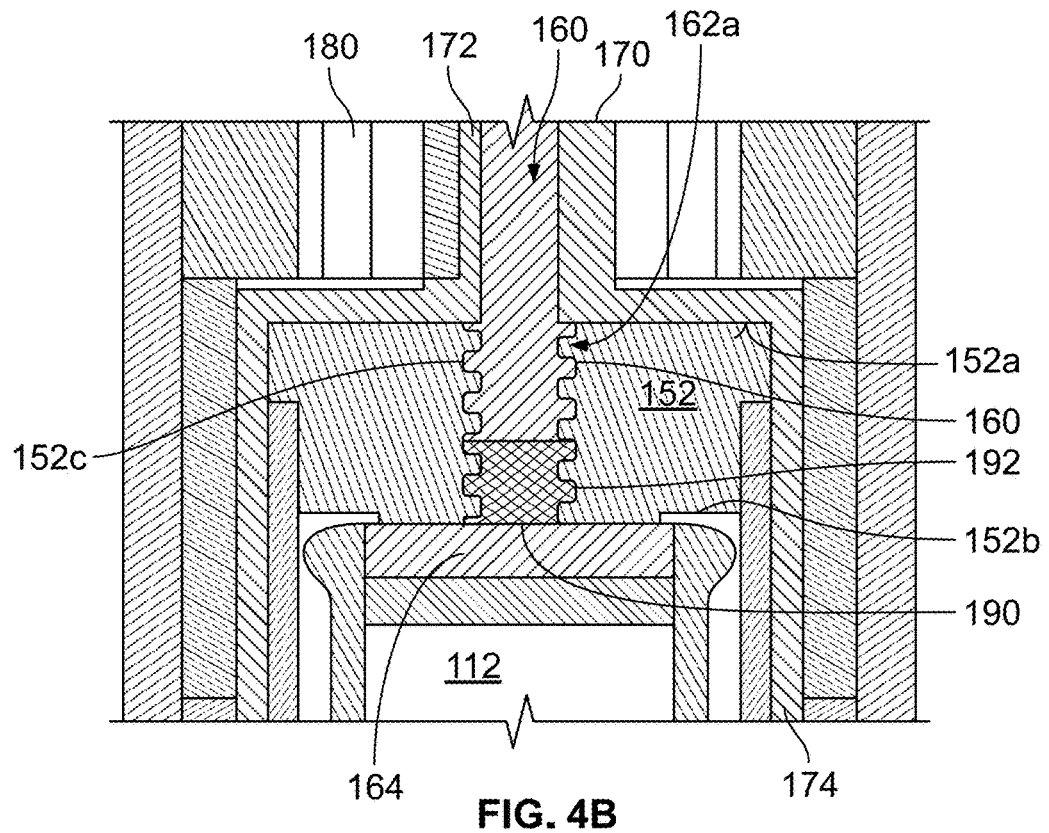
Figure 4C:
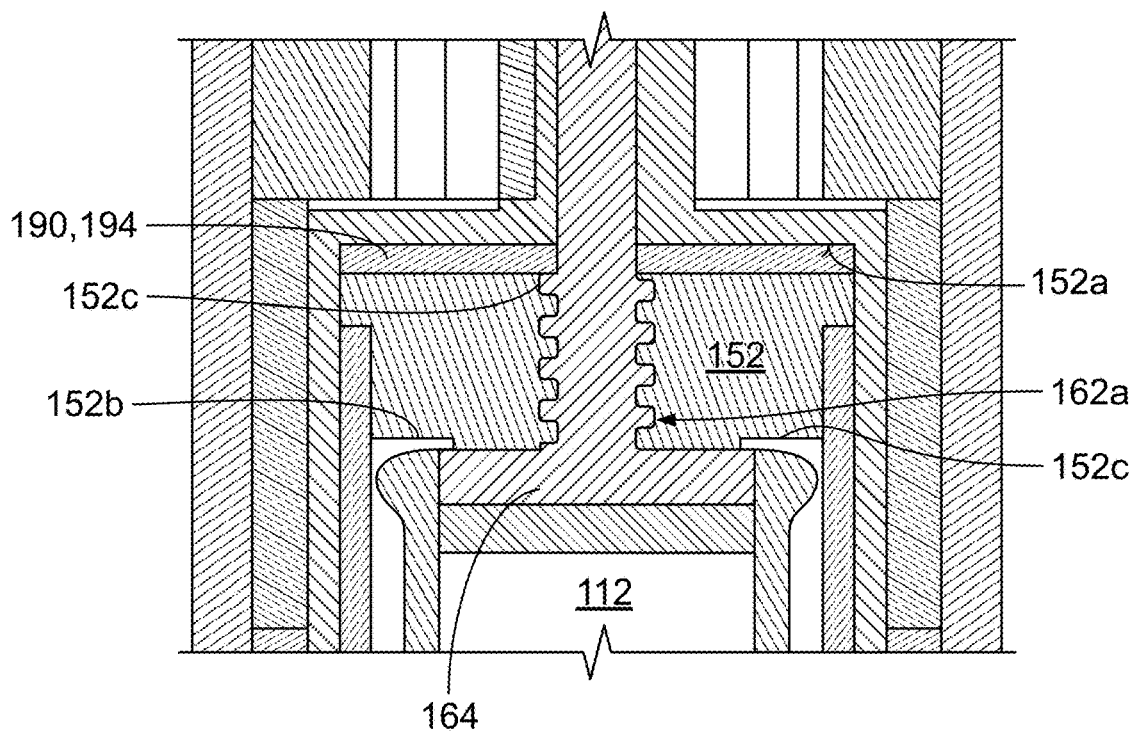

Referring again to FIG. 1 and additionally to FIGS. 4a-4c, the frame member 152 of the actuating mechanism 150 may be fixedly coupled to the housing 102 via any number of approaches. In some arrangements, the frame member 152 may be formed integrally with the housing 102. The frame member 152 may include a first surface 152a, a second surface 152b, and a threaded opening 152c formed between the first surface 152a and the second surface 152b.

The plunger assembly 160 is moveable along the longitudinal axis L of the syringe barrel 112, and includes a plunger rod 162 having a threaded portion 162a which is threadably coupled to and is disposed within the threaded opening 152c of the frame member 152. The threaded portion 162a of the plunger rod 162, and correspondingly, the threaded opening 152c of the frame member 152 may have a thread pitch suitable for any desired drug delivery rate or force/torque combination when driven by the torque spring 180. Relative rotation between the plunger rod 162 and the frame member 152 causes the plunger rod 162 to advance axially. The plunger assembly 160 further includes a plunger face 164 that is disposed near the first end 112a of the syringe barrel 112.

The plunger rod guide 170 includes a rod portion 172 and a cup portion 174 coupled thereto. The rod portion 172 of the plunger rod guide 170 is coupled to the plunger assembly 160 via any number of approaches including, for example, via a splined connection or slotted arrangement that allows for the plunger assembly 160 to be axially displaced relative to the plunger rod guide 170. As such, the plunger rod guide 170 guides rotational movement of the plunger assembly 160. In some examples, the cup portion 174 of the plunger rod guide 170 is adapted to at least partially surround and rotate about the frame member 152 and assists with maintaining alignment of the interconnected moving components. In other examples, the cup portion 174 needn't surround the frame member 152, rather, damping components may be axially aligned with each other. In other words, the cup portion 174 may take any suitable shape or configuration. In these examples, relative motion between the damping components and the cup portion 174 may provide adequate damping forces.

An inner portion 180a of the torque spring 180 is coupled to the rod portion 172 of the plunger rod guide 170 via any known approach to exert a force on the plunger rod guide 170 causing the plunger rod guide 170 to rotate about axis L. In some examples, the torque spring 180 may have a high number of turns to provide an appropriate rotational travel required to expel the medicament from the syringe barrel 112, however, additional parameters of the spring design may influence its torque output such as material properties and any applied heat treatments. The pre-shaping of the torque spring 180 may also impact its performance. As an example, in an autoinjector, a pre-stressed spring may be preferred, because the pre-stressing process generally increases torque output of the spring by initial coiling the spring in an opposite direction of the intended working condition, thereby causing permanent deformation in the steel band. This deformation maximizes the stresses in the material, thereby causing the torque to increase. Such an increase in torque is beneficial to minimize device size and weight.

In some examples, the torque spring 180 may have between approximately 1 and approximately 30 turns in the wound or loaded configuration, and preferably, approximately 12 turns. In some examples, the total spring turns may be higher due to a margin in both ends of the working range of approximately 20%, which may result in the range being between approximately 1*1.4=1.4 to 30*1.4=42. The dose mechanism turns are derived from the pitch and the required travel length. As previously stated, a smaller pitch is preferred due to requiring a low torque input and activation force. Accordingly, the activation force also will be lower. If a high axial force is not needed, the pitch can be raised and require fewer spring turns, thus allowing the device to be smaller. In some examples, the torque spring 180 may have a number of initial, or preload turns to have a usable torque. After the preload turns, the torque spring 180 is further wound with working turns, or turns that are used in the device during injection. As a non-limiting example, the torque spring 180 may have approximately 2.5 preload turns and approximately 6 working turns. As such, the total number of turns during assembly is approximately 8.5. However, due to potentially large tolerances in the angular positioning of spring terminations, the torque spring 180 may have an initial play before reaching a solid state, and thus may have a total of approximately 10 turns. Devices having different drug volumes and viscosities may need a different average torque generated from the torque spring 180 if the same dosing is desired. The average torque output may be controlled by adjusting the width of the band used for the torque spring 180 (e.g., the axial length of the torque spring 180 when disposed in the device), and maintaining the same number of working turns. Doing so may allow different springs to be used with the same configuration as the device and have similar injection times while the volume and/or viscosity of the drug may be modified.

In some examples, the energy ($E_{FLOW}$) required to expel the drug through a needle is determined by any combination of the drug volume, viscosity, needle flow path dimensions, and the targeted dosing time. The energy ($E_{SPRING}$) that the torque spring 180 delivers may be determined by any combination of the number of working turns (N) and the average spring torque during the working turns (T). The energy delivered by the spring may be calculated using the following formula: $E_{SPRING}=2*90*N*T$. If frictional losses are excluded in the system, the following relationship exists: $E_{FLOW}=E_{SPRING}=2*\pi*N*T$. Accordingly, the following relationship results: $E_{FLOW}/(2*\pi)=N*T$. In other words, to have sufficient energy in the torque spring 180 to expel a given drug in a given volume through a given needle in a given time, the product (N*T) remains constant, and thus the higher torque may be converted to fewer working turns.

The threaded interface between the plunger rod 162 and the frame member 152 provides a translation between the input torque of the torque spring 180 and the output axial force. By providing a torque spring 180 with a high turn count, it will have a lower overall torque as well as a smaller change in start and end torque as compared to a linear spring having comparable gearing specifications or other torsion springs with few turns and a lower pitch. Additionally, the threads of the plunger rod 162 and the frame member 152 can have a lower pitch due to the increase in turn count, while still achieving the same linear motion of the plunger assembly 160. If the thread pitch is low, a smaller input torque is necessary to provide the same output force as a high pitch thread and high torque spring. Accordingly, the high turn count (e.g., between approximately 1 and approximately 30 turns), low torque system described herein allows for reduced activation forces, as the activation force is directly related to the input torque that must be used to drive the plunger assembly 160. Additionally, internal structural forces required to resist the torque from the torque spring 180 during storage (e.g., prior to use) is reduced, thus allowing for smaller injector designs to be used and for less expensive raw materials to be used. Further, the increase in turns can lead to a more flexible dampening system (which will be described in further detail below) due to the increase in velocity between the components thereof. Additionally, the threaded interface between the plunger rod 162 and the frame member 152 allows the threaded plunger rod to be adjusted to accommodate for varying quantities of medicament stored in the syringe barrel. If necessary, the threaded plunger rod 162 may be initially installed at a lower position in injectors 100 having lesser drug product volumes disposed in the syringe barrel 112. Accordingly, the number of unique components is reduced, and variation management is simplified. The threaded plunger rod 162 may also be adjustably installed at various depths during the manufacturing and/or assembly process as needed.

Turning to FIGS. 4a-5g, the damper mechanism 190 opposes the torque exerted on the plunger rod guide 170 by the torque spring 180. The damper mechanism 190 can have any number of configurations. For example, FIGS. 4a and 5a illustrate a damper mechanism 190a in the form of a viscous fluid being disposed in an area between an inner surface 102a of the housing 102 and an outer surface 174a of the cup portion 174 of the plunger rod guide 170. The viscous fluid 190a may be disposed at any location along the area between the housing 102 and the cup portion 174, and in some examples may be contained in an area or chamber 190b. It is understood that the chamber 190b may be sealed in some embodiments, and in other embodiments, the chamber 190b may be unsealed. In some applications, an unsealed chamber may be preferred because sealed viscous dampers inherently introduce frictional resistance, which may not be speed dependent or may actually reduce with higher speeds which is the opposite of the design intent. This means at low speed delivery when the medicament is providing the most resistance the seal may continue to contribute measurable frictional resistance. Unsealed dampers will likely have fewer components and more of the resistive force will behave according to the intent where higher speeds create higher damping force and lower speeds create lower damping force. As illustrated in FIG. 5a, the cup portion 174 may have protrusions 174a that contact the inner surface 102a of the housing 102. These protrusions 174a effectively restrict the viscous fluid within the chamber 190b to reduce or eliminate the possibility of the viscous fluid 190a leaking within the housing 102. It is understood that any number of viscous fluids having varying viscosities may be used to achieve a desired amount of dampening depending on the desired configuration of the injector 100 and the medicament contained within the syringe barrel 112. For example, a "motion control" damping viscous fluid 190a or grease may be provided that has a high viscosity at low shear, resulting in yield stress that allows the viscous fluid 190a to remain stationary during transport while providing sufficient damping during actuation. One example of a suitable damping viscous fluid 190a can include Nyemed 7325, manufactured by Nye Lubricants.

Figure 5A:
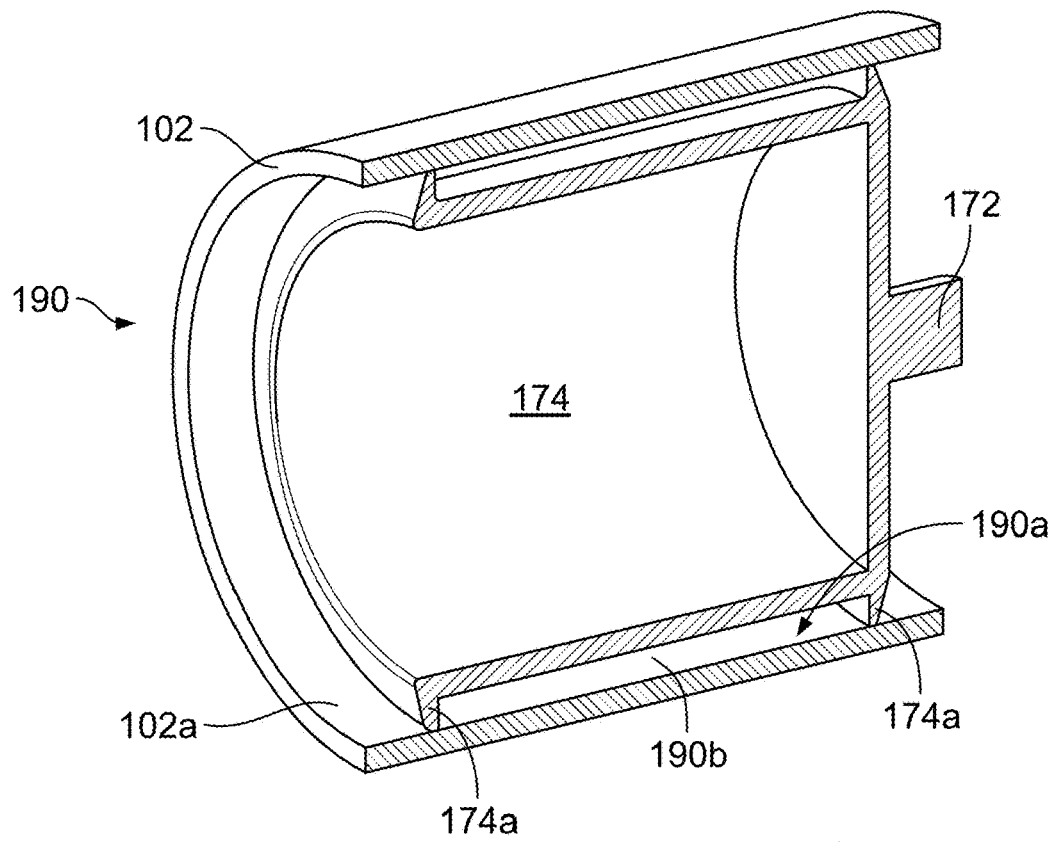
FIGS. 5a-5g illustrate example damper mechanisms of the torque driven injector of FIG. 1 in accordance with various embodiments.
Figure 5B:
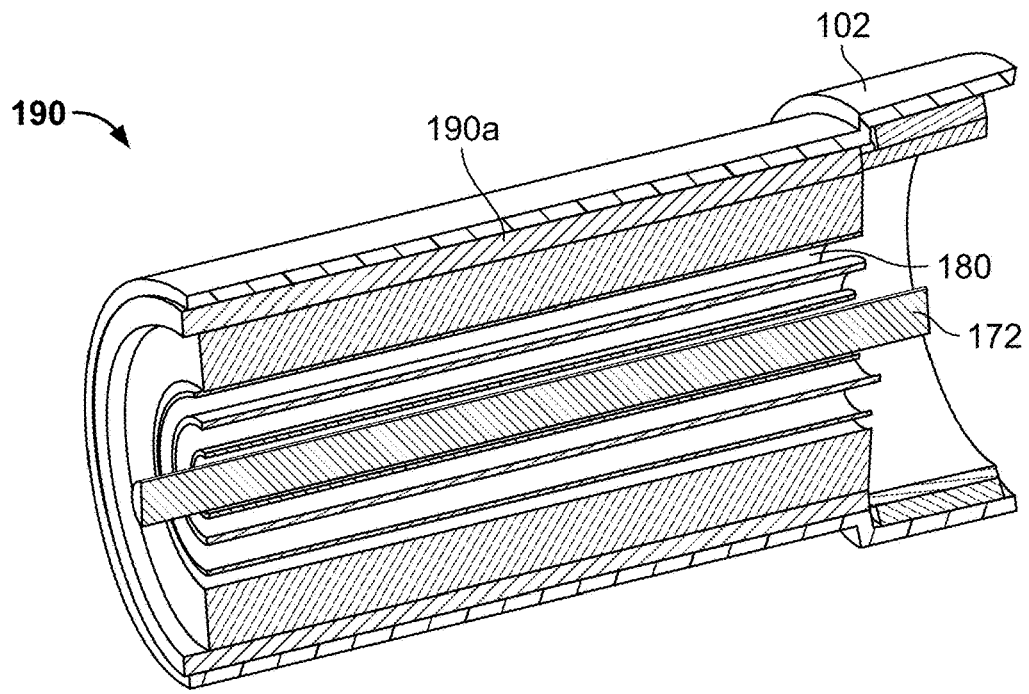

In other examples, and as illustrated in FIG. 5b, the viscous fluid 190a may be disposed at other locations, such as between the housing 102 and the rod portion 172 of the plunger rod guide 170. Further, the viscous fluid may be disposed in a gap between two components having relative motion during extrusion of the medicament such as in the threaded interface between the threaded plunger rod 162 and the frame member 152. In some examples, the length of the gap is at least approximately three times as large as the width of the gap.

Figure 5C:
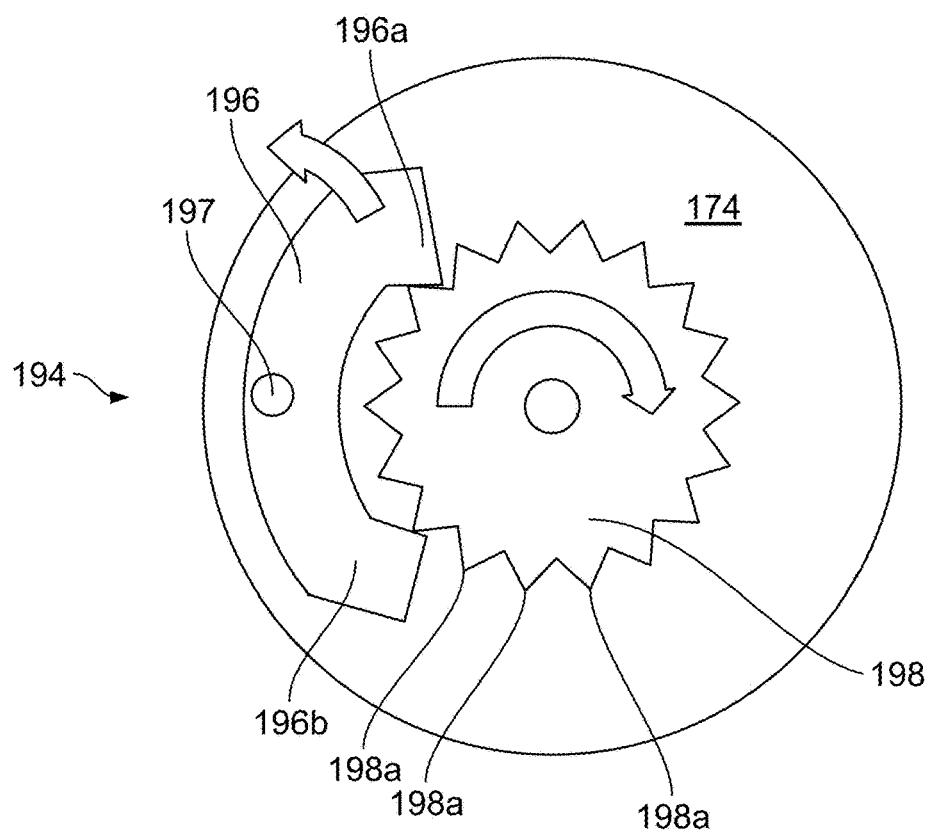
Figure 5D:
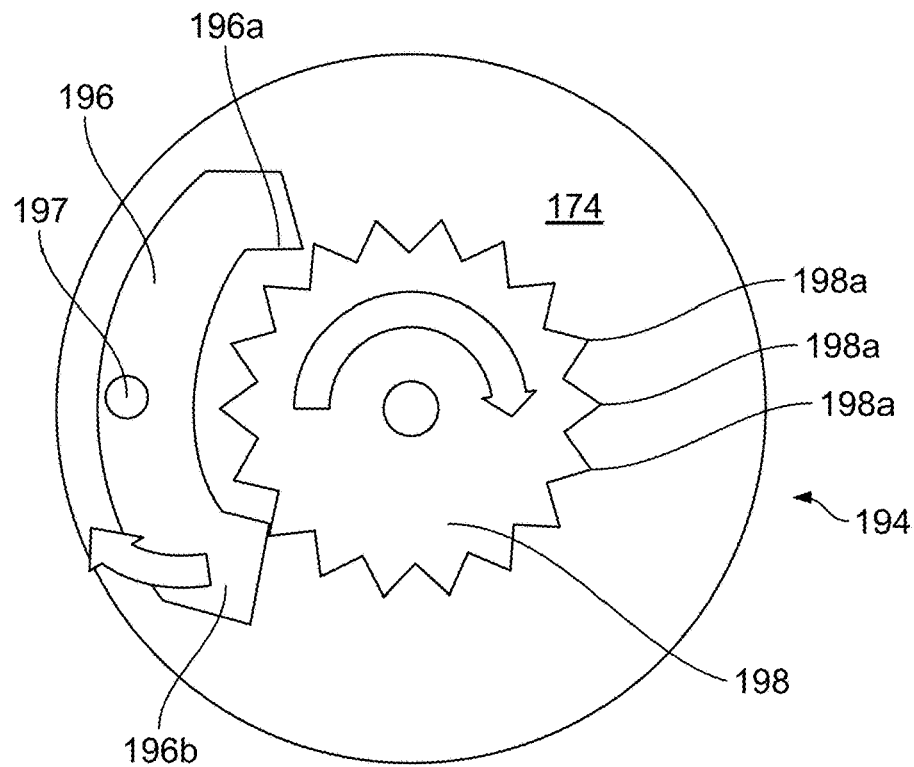
Figure 5E:
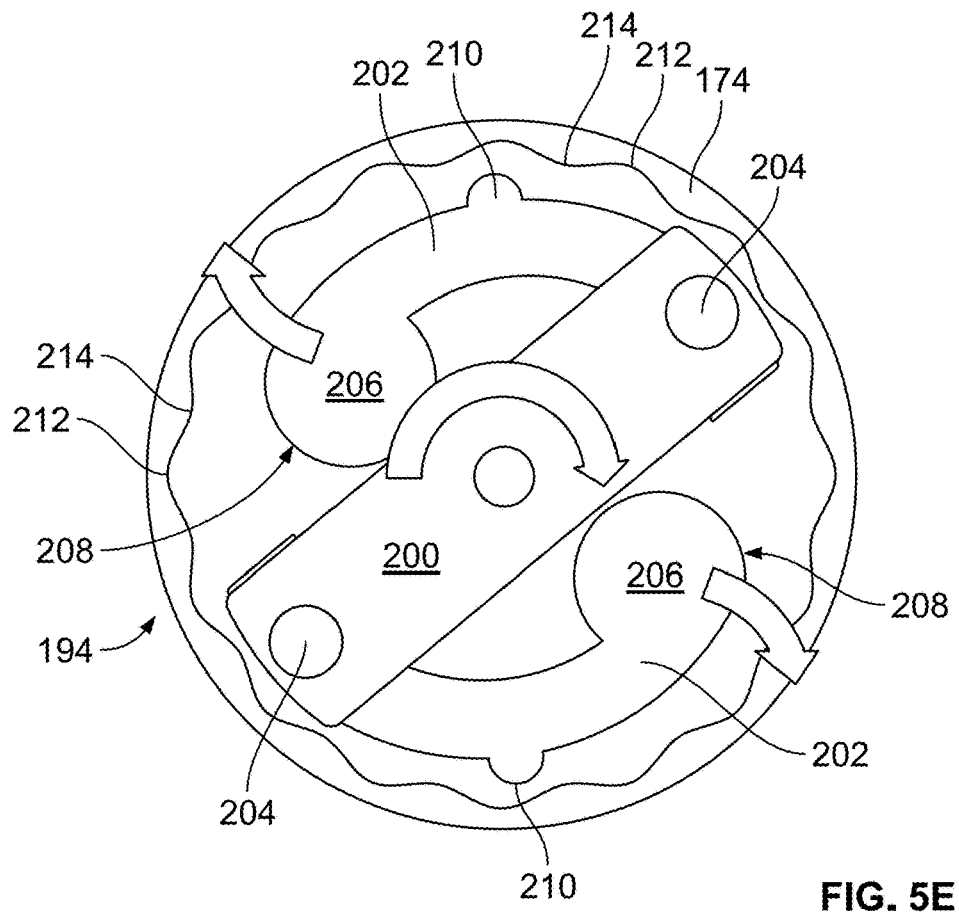
Figure 5F:
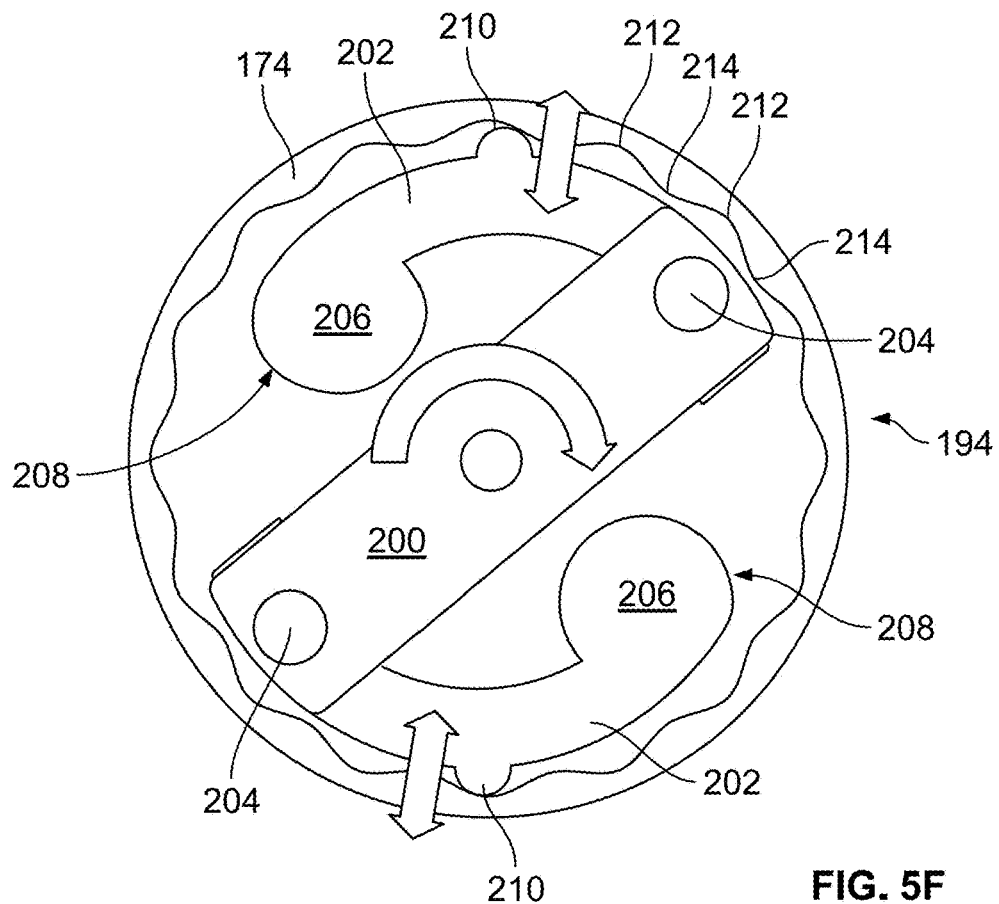
Figure 5G:
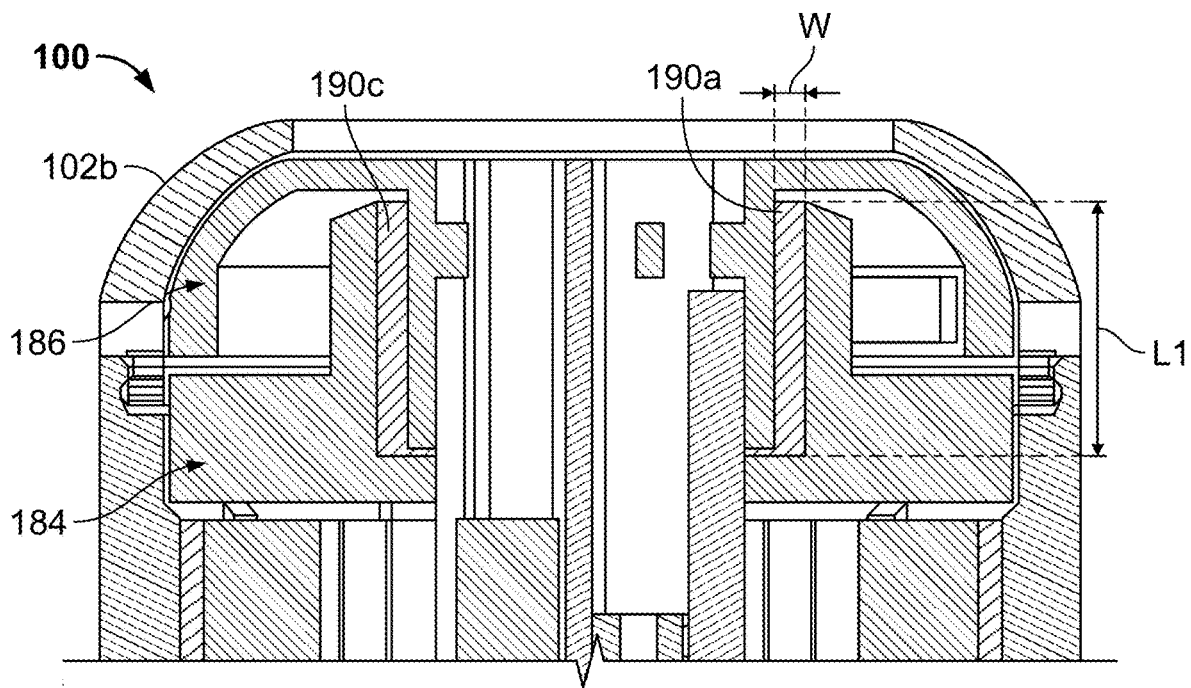
Figure 6:
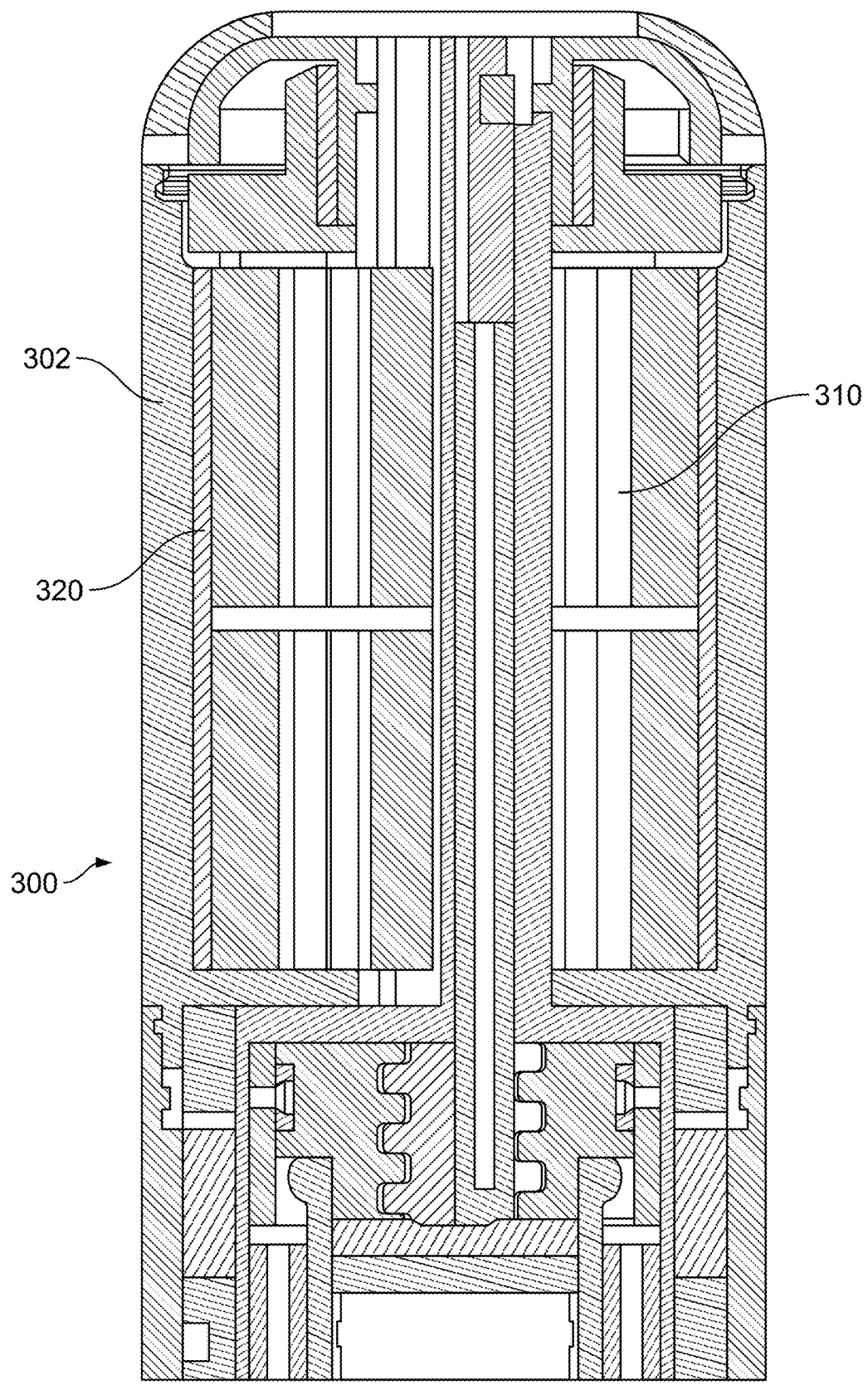
FIG. 6 illustrates an alternate torque driven injector having a spring guide mechanism.

In still other examples, and as illustrated in FIG. 5g, the viscous fluid 190a may be disposed in a void or chamber 190c between an upper frame member 184 and a rotating member 186 disposed in or near a cap 102b of the housing 102. In these examples, the upper frame member 184 is fixed to the housing 102 via any number of approaches. The rotating member 186 may be affixed to the plunger rod guide 170 and/or to the torque spring 180. The void 190c must have a sufficient width (or clearance) denoted as "W" and length denoted as "$L_1$" of engagement to allow for effective damping with less variability than a short, low-clearance interface, which, due to component tolerances and variation, impact damping performance variability. For example, the width of the void may be approximately 1 mm, and the length of engagement may be approximately 8 mm. Other examples are possible. It is understood that in some examples, the upper frame member 184 may include a dosing feedback component that may provide a visual, audible, haptic, and/or other form of feedback to indicate the status and/or the completion of the dose being administered.

In some examples, the damper mechanism 190 may function according to the following mathematical models prior to impact:

Parameters for rotatory viscosity damper torque calculation

| | |
|---|---|
| Inner diameter of damper cylinder surface: | $d_{damper\_inner} := 11.5$ mm |
| Outer diameter of damper cylinder surface: | $d_{damper\_outer} := 13.5$ mm |
| Axial length of damper overlapping surface: | $l_{overlap} := 7.7$ mm |
| Gap between damper surfaces: | $l_{gap} := \dfrac{d_{damper\_outer} - d_{damper\_inner}}{2} = 1$ mm |

| | |
|---|---|
| Effective diameter of damper (mean diameter of cylinders): | $d_{damper} := \dfrac{d_{damper\_outer} + d_{damper\_inner}}{2} = 12.5 \text{ mm}$ |
| Viscosity of damper fluid: | $\mu_{damper} := 22 \text{ Pa} \cdot \text{s} = 220 \text{ poise}$ |
| Viscosity of damper fluid in cPoise: | $\mu_{damper} \cdot 1000 = (2.2 \cdot 10^4) \dfrac{\text{kg}}{\text{m} \cdot \text{s}}$ <br> $\mu_{damper\_fluid} = 0.08 \cdot \text{Pa} \cdot \text{s} = 0.8 \text{ poise}$ |

Supporting parameters for calculation

| | |
|---|---|
| Axial velocity at impact (input from dose time calculation): | $v_{axial\_impact} := 100.0 \cdot \dfrac{\text{mm}}{\text{s}}$ |
| Pitch of thread p: | $p_{thread} := 2.045 \cdot \text{mm}$ |
| Corresponding RPS at impact: | $rps_{damper\_impact} := \dfrac{v_{axial\_impact}}{p_{thread}} = 48.9 \dfrac{1}{\text{s}}$ |
| Corresponding ω at impact: | $\omega_{damper\_impact} := rps_{damper\_impact} \cdot 2 \cdot \pi = 307.246 \dfrac{1}{\text{s}}$ |
| Corresponding u at impact in effective damper diameter: | $u_{damper\_impact} := \omega_{damper\_impact} \cdot \dfrac{d_{damper}}{2} = (1.92 \cdot 10^3) \dfrac{\text{mm}}{\text{s}}$ |
| Rotoric velocity of damper: | $rps_{damper} := rps_{damper\_impact} = 48.9 \dfrac{1}{\text{s}}$ |

Torque as a function of RPS, viscosity and cylinder geometry

The equation for the torque is derived from the theory of Dynamic Viscosity between plates applied on cylinder geometry.

$$T_{damper} := \dfrac{1}{2}\pi^2 \cdot \mu_{damper} \cdot l_{overlap} \cdot d_{damper}^3 \cdot \dfrac{1}{l_{gap}} \cdot rps_{damper} = 79.84 \text{ N} \cdot \text{mm}$$

Rate of shear deformation as a function of cylinder geometry and RPS

The equation for the Rate of shear, $\dfrac{u}{y}$, is derived from the theory of Dynamic Viscosity between plates applied on cylinder geometry.

$$\text{Rate\_of\_shear} := \dfrac{\pi \cdot rps_{damper} \cdot d_{damper}}{l_{gap}} = (1.92 \cdot 10^3) \dfrac{1}{\text{s}}$$

$$u_{control} := \text{Rate\_of\_shear} \cdot l_{gap} = (1.92 \cdot 10^3) \dfrac{\text{mm}}{\text{s}}$$

Shear stress as a function of cylinder geometry and torque

The equation for the shear stress, $\tau$, is derived from the theory of Dynamic Viscosity between plates applied on cylinder geometry.

$$\tau := \dfrac{2 \cdot T_{damper}}{\pi \cdot d_{damper}^2 \cdot l_{overlap}} = 0.042 \dfrac{\text{N}}{\text{mm}^2}$$

$$\tau = (4.225 \cdot 10^4) \dfrac{\text{N}}{\text{m}^2}$$

$$\tau = (4.225 \cdot 10^4) \text{ Pa}$$

Further, the damper mechanism 190 may function according to the following mathematical models after impact and during the dosing stage:

Parameters for rotatory viscosity damper torque calculation

| | |
|---|---|
| Inner diameter of damper cylinder surface: | $d_{damper\_inner} := 11.5 \text{ mm}$ |
| Outer diameter of damper cylinder surface: | $d_{damper\_outer} := 13.5 \text{ mm}$ |
| Axial length of damper overlapping surface: | $l_{overlap} := 7.7 \text{ mm}$ |
| Gap between damper surfaces: | $l_{gap} := \dfrac{d_{damper\_outer} - d_{damper\_inner}}{2} = 1 \text{ mm}$ |
| Effective diameter of damper (mean diameter of cylinders): | $d_{damper} := \dfrac{d_{damper\_outer} + d_{damper\_inner}}{2} = 12.5 \text{ mm}$ |
| Viscosity of damper fluid: | $\mu_{damper} := 60 \text{ Pa} \cdot \text{s} = 600 \text{ poise}$ |
| Viscosity of damper fluid in cPoise: | $\mu_{damper} \cdot 1000 = (6 \cdot 10^4) \dfrac{\text{kg}}{\text{m} \cdot \text{s}}$ <br> $\mu_{damper\_fluid} = 0.08 \cdot \text{Pa} \cdot \text{s} = 0.8 \text{ poise}$ |

Supporting parameters for calculation

| | |
|---|---|
| Axial velocity at dosing (input from dose time calculation): | $v_{axial\_dosing} := 2.0 \cdot \dfrac{\text{mm}}{\text{s}}$ |
| Pitch of thread p: | $p_{thread} := 2.04 \cdot \text{mm}$ |
| Corresponding RPS at dosing: | $rps_{damper\_dosing} := \dfrac{v_{axial\_dosing}}{p_{thread}} = 0.98 \dfrac{1}{\text{s}}$ |
| Corresponding ω at dosing: | $\omega_{damper\_dosing} := rps_{damper\_dosing} \cdot 2 \cdot \pi = 6.16 \dfrac{1}{\text{s}}$ |
| Corresponding u at effective damper diameter: | $u_{damper\_dosing} := \omega_{damper\_dosing} \cdot \dfrac{d_{damper}}{2} = 38.5 \dfrac{\text{mm}}{\text{s}}$ |
| Rotoric velocity of damper: | $rps_{damper} := rps_{damper\_dosing} = 0.98 \dfrac{1}{\text{s}}$ |

Torque as a function of RPS, viscosity and cylinder geometry

The equation for the torque is derived from the theory of Dynamic Viscosity between plates applied on cylinder geometry.

$$T_{damper} := \dfrac{1}{2}\pi^2 \cdot \mu_{damper} \cdot l_{overlap} \cdot d_{damper}^3 \cdot \dfrac{1}{l_{gap}} \cdot rps_{damper} = 4.366 \text{ N} \cdot \text{mm}$$

Rate of shear deformation as a function of cylinder geometry and RPS

The equation for the Rate of shear, $\dfrac{u}{y}$, is derived from the theory of Dynamic Viscosity between plates applied on cylinder geometry.

$$\text{Rate\_of\_shear} := \dfrac{\pi \cdot rps_{damper} \cdot d_{damper}}{l_{gap}} = 38.5 \dfrac{1}{\text{s}}$$

$$u_{control} := \text{Rate\_of\_shear} \cdot l_{gap} = 38.5 \dfrac{\text{mm}}{\text{s}}$$

Shear stress as a function of cylinder geometry and torque

The equation for the shear stress, $\tau$, is derived from the theory of Dynamic Viscosity between plates applied on cylinder geometry.

$$\tau := \dfrac{2 \cdot T_{damper}}{\pi \cdot d_{damper}^2 \cdot l_{overlap}} = 0.002 \dfrac{\text{N}}{\text{mm}^2}$$

$$\tau = (2.31 \cdot 10^3) \dfrac{\text{N}}{\text{m}^2}$$

$$\tau = (2.31 \cdot 10^3) \text{ Pa}$$

Accordingly, the damper mechanism 190 creates more damping prior to impact, and relatively less damping during dose delivery.

In some examples, and as illustrated in FIG. 4b, the damper mechanism 190 may be in the form of a deformation region 192 disposed at the end of the plunger rod 162, which deforms as the plunger assembly 160 advances towards the syringe barrel 112. While the deformation region 192 is illustrated as being located near where the plunger rod 162 intersects or couples to the plunger face 164, the deformation region 192 may be any portion or portions of the plunger assembly 160 including on the plunger face 164, itself near a portion where a leading surface of the plunger face contacts the syringe barrel 112, and/or any interface in the axial and/or rotary force loop having a high inertia and kinetic energy. The purpose of the deformation region 192 is to extend impact time, thereby reducing impact forces and stresses in components to reduce and/or avoid failure. So configured, the mass of the plunger face 164 will create a limited and strongly reduced impact shock upon contacting the syringe barrel 112. This deformation region 192 may be constructed from a different material than the remainder of the plunger assembly 160. For example, the deformation region 192 may be constructed from a "softer" or more pliable material that can absorb the impact between the plunger face 164 and the syringe barrel 112. Example materials may include a foam, an elastomer, a crushable honeycomb or 3D lattice structure, etc. So configured, when the plunger rod 162 advances such that the plunger face 164 impacts a portion of the syringe barrel 112 (such as a stopper), the deformation region 192 collapses to dampen the effects of the impact force.

In some examples (not illustrated), the plunger rod 162 may have a deformable retainer coupled thereto to retain the position of the plunger rod 162 within the housing 102. The deformable retainer may slow the plunger rod for a specified number of revolutions (e.g., between 1 and 3 revolutions) before releasing (e.g., breaking). Accordingly, the deformable retainer will dampen the torque or force exerted by the torque spring 180, and will cease to act as a damper upon breaking.

In some examples, and as illustrated in FIGS. 4c and 5c-5f, the damper mechanism 190 is in the form of a rotating damping device 194. In the illustrated example, the rotating damping device 194 is disposed under a surface of the cup portion 174 of the plunger rod guide 170. Specifically, FIGS. 5c and 5d illustrate a rotating damping device 194 having an anchor 196 that rocks about a pivot 197 as a central push wheel 198 rotates. As the central push wheel 198 rotates with the plunger rod guide 170, individual splines 198a alternatively contact a first side 196a and a second side 196b of the anchor 196. This rocking motion creates continuously reversing acceleration, which in turn dampens the torque exerted by the torque spring 180. The amount of damping force may be adjusted by altering a rocking angle of the anchor 196, a moment of inertial of the anchor 196, and an angular velocity of the central push wheel 198. As the central push wheel 198 spins faster, the rocking rate of the anchor 196 also increases, which in turn increases the continuously reversing acceleration, thereby providing a greater dampening force. In other examples, the rotating damping device 194 may be any number of components having relative moving elements such as the plunger rod 162 and the frame member 152.

In the examples illustrated in FIGS. 5e and 5f, the rotating damping device 194 is in the form of a centrifugal damper assembly that includes a central member 200 and a number of arms 202 that rotate about respective pivots 204. Each of the arms 202 has a weighted portion 206 disposed at distal ends 208 thereof. Each of the arms 202 also include protrusions 210. In this example, the inner surface or rim of the cup portion 174 of the plunger rod guide 170 remains fixed relative to the central member 200 and has a number of alternating recesses 212 and protrusions 214. As illustrated in FIG. 5f, when the plunger rod guide 170 rotates, a centrifugal force causes the weighted portion 206 and thus the arms 202 to move outwardly towards the cup portion 174. Accordingly, the protrusions 210 of each of the arms 202 contact the alternating protrusions 214 and recesses 212 of the cup portion 174 which in turn creates friction to create a dampening force. In this example, the amount of dampening will depend on the angular velocity exerted by the plunger rod guide, as the weighed portions 206 will push harder towards the cup portion 174 with increased angular velocity.

It is understood that any number of alternative rotating devices may be used to create a damping force or torque. Additionally, the mass of the torque spring 180, combined with inertial forces, also provides a dampened motion, as this mass must be accelerated. The resulting acceleration is thereby reduced. As another example, the rotating damping device 194 may be a fly wheel damper (not illustrated) that rotates and absorbs energy delivered by the torque spring 180 during initiation and rotation.

So configured, when the injector 100 is actuated, the torque spring 180 begins to unwind, thus exerting a torque on the plunger rod guide 170 which causes it to rotate about the axis L. Continued rotation of the plunger rod guide 170 causes the plunger assembly 160 to advance towards the syringe barrel 112, thus urging the medicament through the optional filter mechanism 120 and the needle assembly 114 while the filter mechanism 120 acts to restrict particles disposed within the medicament from passing through the needle assembly 114. While the plunger rod guide 170 rotates, the damper mechanism 190 exerts an opposing force on the plunger rod guide 170 and/or any of the moving elements to reduce and/or eliminate any "jerks," "slaps," or "bumps".

Turning to FIGS. 6-8b an alternate injector 300 is provided. It is understood that the injector 300 may include any number of features and/or components described with regard to the injector 100 of FIGS. 1-5g. The injector 300 includes a housing 302 and a torque spring 310 that is guided by a spring guide 320 to improve actuation efficiency and consistency. The spring guide 320 may be in the form of a leaf spring or bridle that is coupled to an outer end 312 of the torque spring 310 to increase torque, assist in unwinding the torque spring 310, reduce hysteresis, and improve cycle life of the torque spring 310. Further, the spring guide may assist with ensuring proper concentric release with the torque spring 310.

Figure 7:
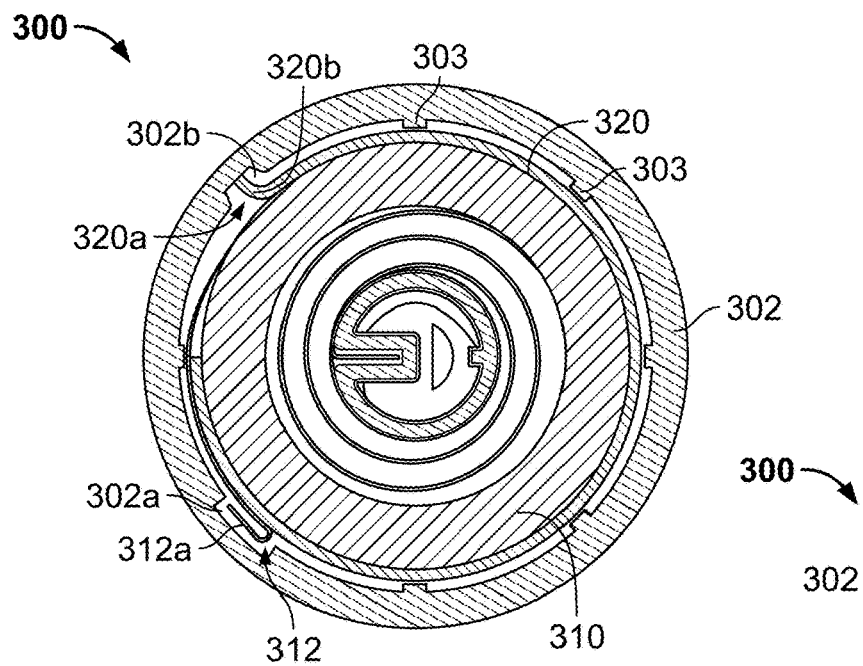
FIG. 7 illustrates a cross sectional view of the example torque driven injector of claim 6.

As illustrated in FIG. 7, the spring guide 320 causes the outer end 312 of the torque spring 310 to be pressed outwardly towards the housing 302, which may include any number of guiding protrusions 303. The outer end 312 of the torque spring 310 includes a bent portion 312a. The housing 302 includes a first notch 302a to accommodate the bent portion 312a of the torque spring 310. So configured, because the spring guide 320 exerts an outward force on the outer end 312 of the torque spring 310, the bent portion 312a is retained in the first notch 302a.

The spring guide 320 may be coupled to the housing using any number of approaches. For example, as illustrated in FIG. 7, an end 320a of the spring guide may include a bent portion 320b that is retained in a second notch 302b of the housing 302. Further, the spring guide 320 may fixed to the housing 302 and/or may be coupled to a post disposed inside or outside of the housing 302. Other examples are possible.

Figure 8A:
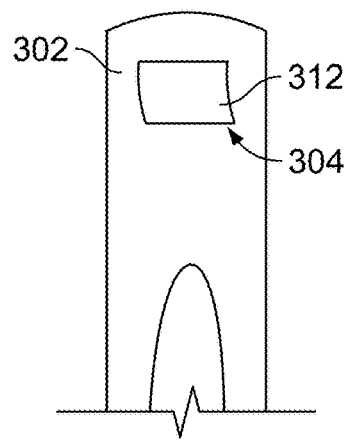
FIGS. 8a and 8b illustrate a torque driven injector having an alternative spring guide mechanism in accordance with various embodiments.
Figure 8B:
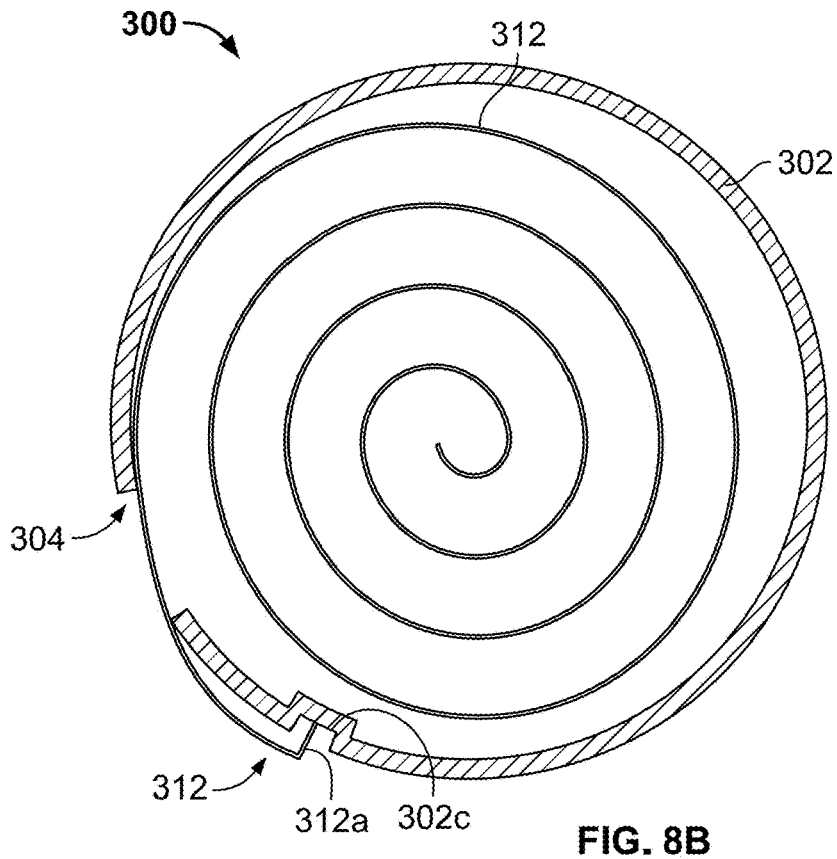

In other examples, and as illustrated in FIGS. 8a and 8b, the housing 302 may itself act as a spring guide 320'. In these examples, the housing 302 includes an opening 304. The outer end 312 of the torque spring 310 may pass through the opening 304, and the bent portion 312a of the torque spring 310 may be retained in a third notch 302c. In some examples, the third notch 302c may be replaced by a second opening (not shown) in which the torque 310 may be threaded therethrough. It is understood that the configuration of the outer end 312 of the torque spring 310 may be modified as needed in order to secure the torque spring to the housing 302 and/or the spring guide 320.

Figure 9:
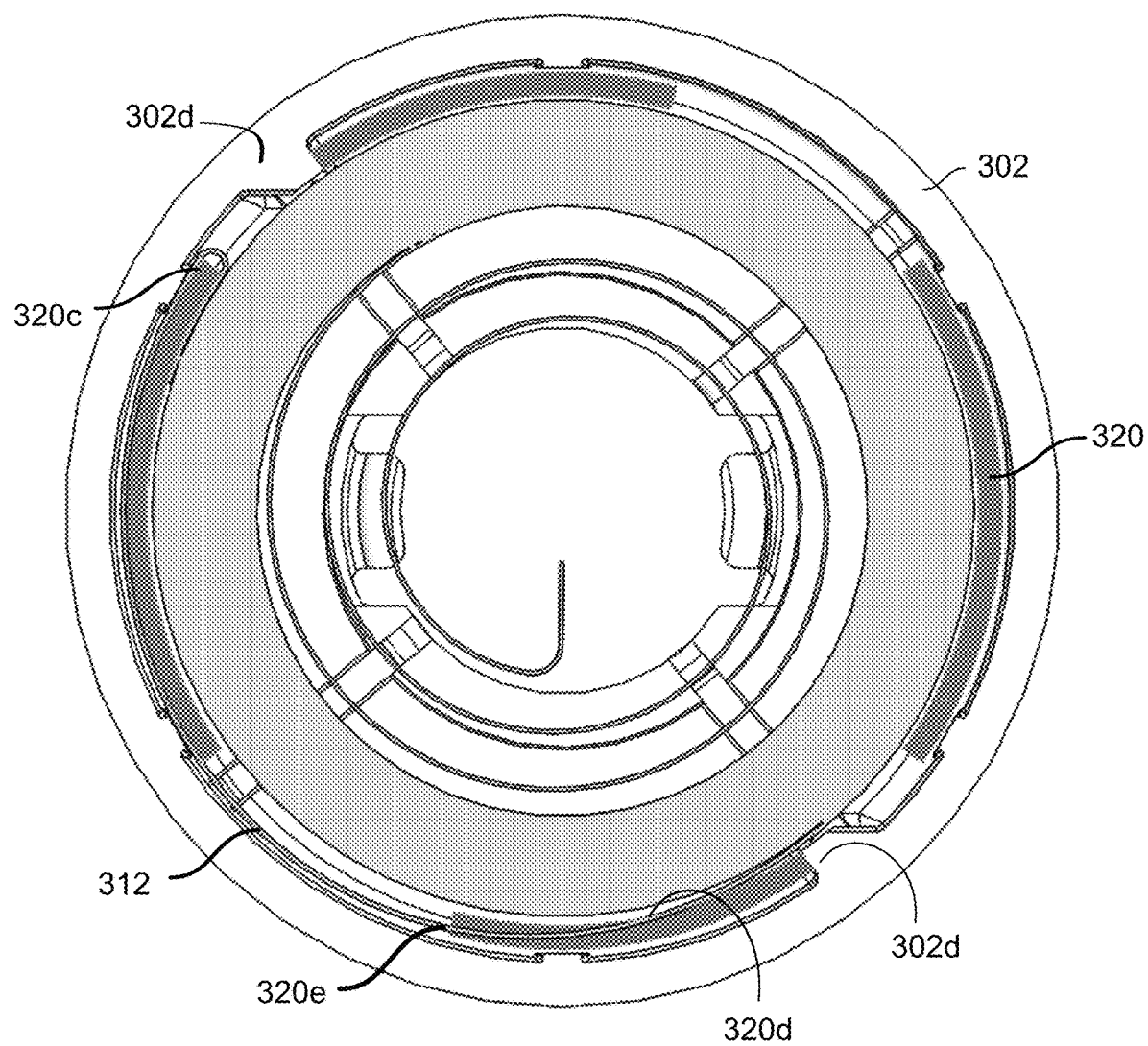
FIG. 9 illustrates a torque driven injector having an alternative spring guide mechanism in accordance with various embodiments.

In yet other examples, and as illustrated in FIG. 9, the spring guide 320 is coupled and/or constrained to the housing 302 via ribs 302d formed by the housing 302. The torque spring 312 enters a portion the spring guide 320 at a first slot or opening 320d, and exits the spring guide 320 at a second slot or opening 320e. The end 312b of the torque spring 312 is then hooked around a slot or opening 320c in the spring guide 320, thereby eliminating the need for cut outs in the housing 302 which may create weak spots in the housing 302, leading to potential deformation, deflection, and/or the risk of breakage when under high stresses.

While the foregoing description provides multiple different "embodiments" for the type of damper mechanisms that may be incorporated into the torque drive system disclosed herein, it should be appreciated that the different damper mechanisms could also be combined with each other, as desired. That is, a person of ordinary skill would understand that a viscous damping system disclosed herein (e.g., FIGS. 4a-4c and 5g) could be combined with a mechanical damping system (e.g., FIGS. 5c-5f) disclosed herein.

The above description describes various systems and methods for use with a drug delivery device. It should be clear that the system, drug delivery device or methods can further comprise use of a medicament listed below with the caveat that the following list should neither be considered to be all inclusive nor limiting. The medicament will be contained in a syringe barrel. In some instances, the syringe barrel is a primary container that is either filled or pre-filled for treatment with the medicament. The primary container can be a cartridge or a pre-filled syringe.

For example, the drug delivery device or more specifically the syringe barrel of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications: U.S. Pat. Nos. 4,703,008; 5,441,868; 5,547,933; 5,618,698; 5,621,080; 5,756,349; 5,767,078; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858 as well as erythropoietin molecules or variants or analogs thereof as disclosed in the following patents or patent applications: U.S. Pat. Nos. 4,703,008; 5,441,868; 5,547,933; 5,618,698; 5,621,080; 5,756,349; 5,767,078; 5,773,569; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgrastim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713 including OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4.;

Myostatin binding proteins, peptibodies, and related proteins, and the like, including myostatin specific peptibodies, particularly those described in U.S. Publication No. 2004/0181033 and PCT Publication No. WO 2004/058988, particularly in parts pertinent to myostatin specific peptibodies, including but not limited to peptibodies of the mTN8-19 family, including those of SEQ ID NOS:305-351, including TNS-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631.;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1.;

Interleukin 1-receptor 1 ("IL1-R1") specific antibodies, peptibodies, and related proteins, and the like, including but not limited to those described in U.S. Publication No. 2004/097712, in parts pertinent to IL1-R1 specific binding proteins, monoclonal antibodies in particular, especially, without limitation, those designated therein: 15CA, 26F5, 27F2, 24E12, and 10H7.

Ang2 specific antibodies, peptibodies, and related proteins, and the like, including but not limited to those described in PCT Publication No. WO 03/057134 and U.S. Publication No. 2003/0229023, particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AbIF; AbIK, AbIP; and AbIP, in their various permutations as described therein.

NGF specific antibodies, peptibodies, and related proteins, and the like including, in particular, but not limited to those described in U.S. Publication No. 2005/0074821 and U.S. Pat. No. 6,919,426, particularly as to NGF-specific antibodies and related proteins in this regard, including in particular, but not limited to, the NGF-specific antibodies therein designated 4D4, 4G6, 6H9, 7H2, 14D10 and 14D11;

CD22 specific antibodies, peptibodies, and related proteins, and the like, such as those described in U.S. Pat. No. 5,789,554, to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof.

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid HCA (y4), deposited at the ATCC under number PTA-5214, and a light chain encoded by a polynucleotide in plasmid LCF (K), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein).

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, as disclosed in the foregoing publication and in Thakur et al. (1999), Mol. Immunol. 36:1107-1115. In addition, description of the properties of these antibodies provided in the foregoing publication. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431 as to TALL-1 binding proteins, particularly the molecules of Tables 4 and 5B.;

Parathyroid hormone ("PTH") specific antibodies, peptibodies, and related proteins, and the like, such as those described in U.S. Pat. No. 6,756,480, particularly in parts pertinent to proteins that bind PTH;

Thrombopoietin receptor ("TPO-R") specific antibodies, peptibodies, and related proteins, and the like, such as those described in U.S. Pat. No. 6,835,809, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No.

7,220,410 and OA-5d5 described in U.S. Pat. Nos. 5,686,292 and 6,468,529 and in PCT Publication No. WO 96/38557, particularly in parts pertinent to proteins that bind HGF;

TRAIL-R2 specific antibodies, peptibodies, related proteins and the like, such as those described in U.S. Pat. No. 7,521,048, particularly in parts pertinent to proteins that bind TRAIL-R2;

Activin A specific antibodies, peptibodies, related proteins, and the like, including but not limited to those described in U.S. Publication No. 2009/0234106, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, particularly in parts pertinent to proteins that bind TGF-beta;

Amyloid-beta protein specific antibodies, peptibodies, related proteins, and the like, including but not limited to those described in PCT Publication No. WO 2006/081171, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Solids™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgrastim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 14667-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNa mAb (MEDI-545, MDX-1103); anti-IGF1R mAb; anti-IGF-1R mAb (HuMax-Inflam); anti-IL12 mAb (ABT-874); anti-IL12/1L23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications: U.S. Pat. No.

8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BITE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug injection device, drive damper mechanisms, systems, methods, and elements thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention.

It should be understood that the legal scope of the invention is defined by the words of the claims set forth at the end of this patent. The appended claims should be construed broadly to include other variants and embodiments of same, which may be made by those skilled in the art without departing from the scope and range of equivalents of the device, drive damper mechanisms, systems, methods, and their elements.

What is claimed is:

1. An injector comprising:
a housing having a syringe assembly and an actuating mechanism at least partially disposed within the housing,
the syringe assembly including:
a syringe barrel having a first end, a second end, and a longitudinal axis, the syringe barrel adapted to store a medicament for patient administration, and
a needle assembly coupled to the second end of the syringe barrel, the needle assembly having a needle hub and a needle attached thereto,
the actuating mechanism being operatively coupled to the syringe assembly and including:
a frame member disposed within the housing, the frame member having a threaded opening formed between a first surface and a second surface,
a plunger assembly comprising a threaded plunger rod and a plunger face, the threaded plunger rod threadably coupled to the threaded opening of the frame member, the plunger face being disposed near the first end of the syringe barrel, the plunger assembly being moveable along the longitudinal axis of the syringe barrel,
a plunger rod guide coupled to the plunger assembly to maintain alignment between at least the frame member and the plunger assembly, and
a torque spring configured to exert a torque and cause relative rotation between at least one of (a) the plunger assembly and the frame member or (b) the plunger rod guide and the frame member, wherein relative rotation causes the plunger assembly to advance towards the syringe barrel to urge the medicament through the needle assembly.

2. The injector of claim 1, further comprising at least one of (a) or (b):
(a) a filter member disposed adjacent to the needle hub, wherein the filter member restricts particles dispersed within the medicament from entering the needle assembly,
(b) a damper mechanism that dampens an effect of the torque spring, the damper mechanism formed by at least one of the frame member, the plunger assembly, and the plunger rod guide, wherein upon the torque spring exerting a torque on the plunger rod guide, the damper mechanism exerts an opposing force on the plunger rod guide.

3. The injector of claim 2, wherein the injector further comprises (a), and wherein the filter member includes a plurality of openings to allow the medicament to pass through while restricting particles dispersed within the medicament from passing through, wherein the plurality of openings have a diameter of between approximately 10 µm and approximately 50 µm.

4. The injector of claim 2, wherein the injector further comprises (a), and wherein the filter member comprises a plurality of openings to allow the medicament to pass through while restricting particles dispersed within the medicament from passing through, wherein the plurality of openings have a generally conical shape.

5. The injector of claim 2, wherein the injector further comprises (a), and wherein the filter member is at least partially disposed within a portion of the needle hub.

6. The injector of claim 2, wherein the injector further comprises (a), and wherein the filter member is at least partially disposed within an opening defined by the second end of the syringe barrel.

7. The injector of claim 2, wherein the injector further comprises (a), and wherein the filter member occupies an entire diameter of the syringe barrel.

8. The injector of claim 2, wherein the injector further comprises (b), and wherein the damper mechanism comprises a viscous material disposed between a portion of the plunger rod guide and the housing.

9. The injector of claim 8, wherein the damper mechanism comprises a sealed or unsealed chamber formed between a portion of the plunger rod guide and the housing.

10. The injector of claim 2, wherein the injector further comprises (b), and wherein the damper mechanism comprises a deformation region disposed on the plunger rod and adapted to at least partially deform as the plunger assembly advances towards the syringe barrel.

11. The injector of claim 2, wherein the injector further comprises (b), and wherein the damper mechanism comprises a rotating damping assembly disposed between the plunger rod guide and the plunger assembly.

12. The injector of claim 11, wherein the rotating damping assembly comprises a rocking anchor that rocks about a central push wheel to create a continuously reversing acceleration as the torque spring exerts torque.

13. The injector of claim 11, wherein the rotating damping assembly comprises a weighted centrifugal damper assembly that contacts a fixed surface to create friction as the torque spring exerts torque.

14. An actuating mechanism for an injector, the injector comprising a housing having a syringe assembly at least partially disposed within the housing and adapted to being coupled to the actuating mechanism, the actuating mechanism comprising:
   a frame member adapted to be disposed within the housing, the frame member having a threaded opening formed between a first surface and a second surface;
   a plunger assembly comprising a threaded plunger rod and a plunger face, the threaded plunger rod threadably coupled to the threaded opening of the frame member, the plunger face being disposed near the syringe assembly;
   a plunger rod guide coupled to the plunger assembly to maintain alignment between at least the frame member and the plunger assembly;
   a torque spring configured to exert a torque and cause relative rotation between at least one of (a) the plunger assembly and the frame member or (b) the plunger rod guide and the frame member; and
   a damper mechanism that dampens an effect of the torque spring, the damper mechanism formed by at least one of the frame member, the plunger assembly, and the plunger rod guide;
   wherein upon the torque spring exerting a torque, the damper mechanism exerts an opposing force to reduce an impact force between the plunger assembly and the syringe assembly.

15. The actuating mechanism of claim 14, wherein the damper mechanism comprises at least one of (a) through (e): (a) a viscous material disposed between a portion of the plunger rod guide and the housing, (b) a sealed or unsealed chamber formed between a portion of the plunger rod guide and the housing, (c) a deformation region adapted to at least partially deform as the plunger assembly advances towards the syringe barrel, (d) a rotating damping assembly disposed between the plunger rod guide and the plunger assembly, or (e) a viscous material disposed between at least one of a portion of the plunger rod guide, the plunger rod, the frame member and the housing.

16. The actuating mechanism of claim 15, wherein the damping mechanism comprises (d) and the rotating damping assembly comprises a rocking anchor that rocks about a central push wheel to create a continuously reversing acceleration as the torque spring exerts torque.

17. The actuating mechanism of claim 15, wherein the damping mechanism comprises (d) and the rotating damping assembly comprises a weighted centrifugal damper assembly that contacts a portion of the plunger rod guide to create friction as the torque spring exerts torque.

18. A method of adjusting an actuating mechanism for an injector, the injector comprising a housing having a syringe assembly at least partially disposed within the housing and being coupled to the actuating mechanism, the actuating mechanism comprising:
   disposing a frame member in the housing, the frame member having a threaded opening formed between a first surface and a second surface;
   providing a plunger assembly comprising a threaded plunger rod and a plunger face, the threaded plunger rod threadably coupled to the threaded opening of the frame member, the plunger face being disposed near the syringe assembly;
   placing the threaded plunger rod at a desired depth relative to the frame member, the desired depth corresponding to a quantity of medicament in a syringe barrel of the syringe assembly during manufacturing.

19. The method of claim 18, further comprising:
   coupling a plunger rod guide to the plunger assembly to maintain alignment between at least the frame member and the plunger assembly;
   coupling a torque spring to the plunger rod guide to exert a force to cause relative rotation between at least one of (a) the plunger assembly and the frame member or (b) the plunger rod guide and the frame member; and
   providing a damper mechanism to dampen an effect of the torque spring.

* * * * *